(12) United States Patent
Li et al.

(10) Patent No.: US 6,878,522 B2
(45) Date of Patent: Apr. 12, 2005

(54) METHODS FOR THE IDENTIFICATION OF COMPOUNDS USEFUL FOR THE TREATMENT OF DISEASE STATES MEDIATED BY PROSTAGLANDIN D2

(76) Inventors: Baiyong Li, 20 Elsie La., Clinton, CT (US) 06413; Kuldeep S. Neote, 15 Rose La., East Lyme, CT (US) 06333; Ronald P. Gladue, 83 Rowley Dr., Stonington, CT (US) 06378; John B. Cheng, 5 Farmstead La., Waterford, CT (US) 06385; Paul H. Bauer, 179 Highland Ave., Arlington, MA (US) 02476; Jiansu Zhang, 71 Glencliff Rd., Roslindale, MA (US) 02131

( * ) Notice: Subject to any disclaimer, the term of this patent is extended or adjusted under 35 U.S.C. 154(b) by 260 days.

(21) Appl. No.: 09/833,126

(22) Filed: Apr. 11, 2001

(65) Prior Publication Data

US 2002/0022218 A1 Feb. 21, 2002

Related U.S. Application Data

(60) Provisional application No. 60/257,393, filed on Dec. 22, 2000, and provisional application No. 60/216,796, filed on Jul. 7, 2000.

(51) Int. Cl.[7] ...................... G01N 33/53; G01N 33/567; C07C 59/147; C07C 59/185
(52) U.S. Cl. .................. 435/7.1; 435/7.2; 554/117
(58) Field of Search .................. 435/7.1, 7.2; 554/117

(56) References Cited

U.S. PATENT DOCUMENTS 3,885,041 A    5/1975    Aspinall et al. ............ 424/318

FOREIGN PATENT DOCUMENTS

| EP | 0253094 | 1/1988 | ......... A61K/31/557 |
| EP | 0322153 | 6/1989 | ......... C07D/417/06 |
| JP | WO 01/14882 | 8/2000 | |

OTHER PUBLICATIONS

H. Tsuda, et al., Clin Exp Immunol, vol. 123, pp. 105–111, (2001).
H. Hirai, et al., J. Exp. Med., vol. 193, pp. 255–261, (2001).
Lorenzo Cosmi, et al., Eur. J. Immunol., vol. 30, pp. 2972–2979, (2000).
Kinya Nagata, et al., FEBS Letters, vol. 459, pp. 195–199, (1999).
Hiroyuki Abe, et al., Gene, vol. 227, pp. 71–77, (1999).
Kinya Nagata, et al., The Journal of Immunology, vol. 162, pp. 1278–1286 (1999).
Leitinger, et al., Thrombosis Research, vol. 86, No. 4, pp337–342, 1997.
Bundy, et al., J. Med. Chem. 1983, 26, pp. 790–799.
Flower, et al., Br. J. Pharmac, 1976, 56, pp. 229–233.
Monneret, et al., Jrnl of Pharm. And Experimental Therapeutics, vol. 504, No. 1, pp. 349–355, 2003.
Menciu et al., Jrnl of Medicinal Chem., 1999, vol. 42, No. 4, 638–648.

*Primary Examiner*—Robert Landsman

(57) ABSTRACT

The present invention relates to the discovery that $PDG_2$ is the neutral ligand for orphan receptor CRTH2, which interaction, it will now immediately be recognized, is important in the development of valuable pharmaceuticals. The present invention is therefore related to methods for screening for therapeutic compounds useful in the treatment of $PGD_2$-related disorders such as allergy, asthma and inflammation. Appropriate assay methodology is also disclosed.

11 Claims, 11 Drawing Sheets

Comparison of [3H]PGD$_2$ binding results in human eosinophils and CRTH2 and DP transfectants.

| | CRTH2 transfectant IC50, uM | Human eosinophils IC50, uM | DP transfectant IC50, uM |
|---|---|---|---|
| PGD2 | 0.015 (4) | 0.025 (4) | 0.022 (3) |
| PGF2α | 0.98 (1) | 1.5 (1) | 8.75 (1) |
| PGE2 | 1.6 (1) | 3.3 (1) | 6.76 (1) |
| BW-245C | >100 (3) | >100 (3) | 0.01 (2-3) |

PGD₂ Derivatives

| Structure | Chemical Name | IC50 in Ca flux assay |
|---|---|---|
| (structure) | 13,14-dihydro-15 keto-PGD$_2$ | 26 nM |
| (structure) | 16,16-dimethyl-PGD$_2$ | 16 nM |
| (structure) | 15(S)-15-methyl-PGD$_2$ | 16 nM | under similar circumstances, PGD$_2$ itself tested at about 15.2 nM

FIG. 2

Human CD4 T cells were isolated from PBMC and stimulated with anti-CD3 and/or anti-CD28 for 4 days and chemotaxis assay was performed using PGD2, murine MDC and murine SDF.

Chemotactic response of human basophils to PGD2 and C5a

The structure of two PGD2 antagonists:

PGD2

9a, 11b-PGF2

PGJ2

PGE1

BW-245C

PGE2

PGF2α

PGI2

[4-Chloro-2-(4-chloro-phenylsulfanyl)-phenyl]-acetic acid.
Ratio of CRTH2 $IC_{50}$ to DP $IC_{50}$ is less than 1:40.

4-(3-Acetoxy-4,4,10,13,14-pentamethyl-7-oxo-2,3,4,5,6,7,10,11,12,13,14,
15,16,17-tetradecahydro-1H-cyclopenta[a]phenanthren-17-yl)-pentanoic acid.
Ratio of CRTH2 $IC_{50}$ to DP $IC_{50}$ is less than 1:30.

(1-Benzothiazol-2-ylmethyl-5-fluoro-2-methyl-1H-indol-3-yl)-acetic acid. Ratio of CRTH2 $IC_{50}$ to DP $IC_{50}$ is less than 1:40.

[3-(6-Hydroxy-benzothiazol-2-ylmethyl)-4-oxo-3,4-dihydro-phthalazin-1-yl]-acetic acid. Ratio of CRTH2 $IC_{50}$ to DP $IC_{50}$ is less than 1:20.

METHODS FOR THE IDENTIFICATION OF COMPOUNDS USEFUL FOR THE TREATMENT OF DISEASE STATES MEDIATED BY PROSTAGLANDIN D2

The present application claims priority under 35 USC section 119(e) of U.S. Provisional Application No. 60/257,393 filed Dec. 22, 2000, and also U.S. Provisional Application No. 60/216,796 filed Jul. 7, 2000, the complete text, claims and figures of both applications being incorporated by reference herein, as if fully set forth.

FIELD OF THE INVENTION

The present invention relates to the identification of compounds useful in the treatment and prevention of disease states mediated by prostaglandin D2 ("$PGD_2$").

Prostaglandins are a class of compounds derived from the 20-carbon fatty acid skeleton of arachidonic acid which function as locally acting hormone-like chemical mediators. Prostaglandins define one major division of the eicosanoids, a large family of chemical mediators, derived from 20 carbon-polyunstaturated fatty acids, and which also includes the lipoxins, thromboxanes, hydroperoxy fatty acids, and leukotrienes.

In general, synthesis of eicosanoids is stimulated by local tissue damage, hormonal stimuli, or via cellular activation pathways (such as binding of IgE immunoglobins to cell surface receptors). Unlike stored, pre-formed chemical mediators, eicosanoid lipid mediators typically appear in cells only after activation events. Eicosanoids, in turn, bind to specific cell surface receptors thereby mediating a wide variety of effects in numerous tissues. Prostaglandins are known to mediate many inflammatory responses and functions of the immune system. Antagonist compounds have been developed for various classes of eicosanoids that act to prevent the normal effects of eicosanoid-receptor binding.

Generally speaking, the inflammatory response is a protective mechanism that facilitates response to local injury. For example, leakage of tissue fluids into the affected area facilitates contact with antibodies, and also permits the migration of white blood cells to directly combat any injurious agent. Unfortunately, an inflammatory response may be inappropriate, that is, it may continue for an excessive period of time or involve participation by inflammatory system components that, unfortunately, act to damage to the body, thereby contributing to, or even defining, a disease state. Accordingly, there are numerous circumstances where it is medically appropriate to interefere with inflammatory processes. Allergies and asthma represent a major class of complex, and typically chronic, inflammatory disease. As is typical of many inflammatory disease states, allergic disease states also involve aberrant or otherwise undersired activation of the immune system.

The present invention is particularly directed to the identification of compounds useful in the prevention and treatment of allergic diseases, including allergic asthma, atopic dermatitis, and allergic rhinitis. The present invention is also directed generally to the identification of compounds useful in the prevention and treatment disease states involving inflammatory components including, without limitation, inflammatory disorders such as rheumatoid arthritis, osteoarthritis, inflammatory bowel disease; disorders of the skin including psoriasis, eczema, erythema, pruritis, and acne; stroke, and any disease marked by reperfusion injury, graft rejection, and autoimmune diseases.

REPORTED DEVELOPMENTS

Allergic asthma and allergic rhinitis are diseases that currently affect about 10% of the population, and that number appears to be increasing (Bush, R.K.a.G., John W., Handbook of asthma and rhinitis. 1st ed. 1997, Abingdon: Blackwell Science. 270). Currently numerous classes of pharmaceutical agents are widely used to treat these diseases, for example, antihistamines, decongestants, β2 agonists, anticholinergics, methylxanthines, cromolyns, corticosteroids, and leukotriene modulators. Generally however, the usefulness of these agents is limited by side-effects and low efficacy. Accordingly, there is a critical medical need to identify pharmaceutically active compounds that interfere with key steps of the inflammatory and immunological processes that contribute to these disease states, and other inflammatory conditions.

$PGD_2$ is known to be produced by platelets. It is also produced by mast cells, macrophages, and other cells that participate in inflammatory processes, and processes of the immune system. Reported functions of $PGD_2$ include inhibition of platelet aggregation, relaxation and constriction of smooth muscle, modulation of signal transmission in neurons, sleep induction, and facilitation of the chemotactic response of cells that mediate inflammatory response. Mast cells have long been associated with immunoglobin type IgE-dependent allergic diseases, such as allergic rhinitis and allergic asthma. There is clear evidence that mast cell-derived mediators, such as $PGD_2$, leukotriene $C_4$, histamine, proteases, cytokines and chemokines, contribute to immediate hypersensitivity reactions (for example, see Rossi and Olivieri, Chest, 112(2), pp. 523–529, 1997).

Besides mast cells, immune system helper T cells of type Th2 have been recognized as potential orchestrators of allergic responses (Wills-Karp, 1999, Annual Review of Immunology 17:255–81). In atopic patients, disease severity correlates with the level of Th2-produced cytokines, and Th2 cells have been identified in bronchoalveolar lavage and bronchial biopsy specimens (Robinson et al., 1992, New England Journal of Medicine 326(5):298–304; Walker et al., 1992, American Review of Respiratory Disease 146(1):109–15). Relief of symptoms by corticosteroids correlates well with the reduction of Th2 cytokines (for example, see Wilkinson et al., 1991, International Archives of Allergy & Applied Immunology 94(1–4):220–1). Additionally, adoptive transfer of Th2 cells into IL-4 knockout mice has provided evidence that Th2 cells contribute to the pathogenesis of airway hyperresponsiveness (Li et al., 1996, Journal of Immunology 157(8):3216–9; Brusselle et al., 1995, American Journal of Respiratory Cell & Molecular Biology 12(3):254–9).

However, providing more specific and effective therapies for inflammatory conditions will require a better understanding of the specificity of each involved chemical mediator for cellular receptors, and the nature of resultant downstream signalling events. Although numerous receptors have been identified for prostaglandins (for example, DP, FP and EP), only the DP receptor has been shown to have specificity for $PGD_2$. Given the complexity of biological responses, it is highly likely that additional cellular receptor types for $PGD_2$ should exist, although recent isolation efforts in this regard have failed (see Narumiya et al., 1999, Physiological Reviews 79(4):1193–226).

Recently it has been determined that $PGD_2$ is produced by human Th2 cells (Tanaka K, et al., J Immunol, 164(5) pp. 2277–80, 2000). It has also been determined that Th2 cells express a particular G-protein coupled receptor, originally cloned from a human Th2 cell line (see Nagata et al., 1999, Journal of Immunology 162(3):1278–86, and U.S. Pat. No. 6,040,426, both of which are incorporated by reference herein). This receptor has been termed CRTH2

(chemoattractant receptor-homologous molecule expressed on Th2 cells). See also Gene Bank accession number AB008535.

The CRTH2 receptor is also selectively expressed from a wide variety of tissues including the brain, lung and lymphoid organs (Abe et al., 1999, Gene 227(1):71–7). With respect to expression from immune system cells, it is reported that CRTH2 receptor is selectively expressed on Th2 cells, eosinophils and basophils, but not Th1 cells, B cells and NK cells (Nagata et al., 1999, FEBS Letters 459(2):195–9). Additionally, there is no significant sequence homology between CRTH2 and any other known cell surface proteins, except for a low homology (~30%) with the FMLP receptor. Additionally, no natural ligand for CRTH2 has been reported.

The present invention is directed to the discovery that the natural ligand for CRTH2 is in fact $PGD_2$ which interaction, it will now immediately be recognized, is important in the development of specific anti-inflammatory pharmaceuticals.

SUMMARY OF THE INVENTION

The present invention is directed to methods for screening for therapeutic compounds that are useful in the treatment of $PGD_2$-related disorders, such as allergy, asthma, and inflammation. The invention is based, in part, on the discovery as described herein that $PGD_2$ is a natural ligand for CRTH2, and the role of this interaction in allergic and inflammatory responses. In various embodiments, the invention provides primary screening assays to identify modulators, that is compounds that are antagonists and/or agonists, of $PGD_2$-CRTH2 interactions. These primary assays are adaptable to high-throughput screening.

In other embodiments, the invention provides secondary assays to further characterize the biological activity of such modulators (for example agonist or antagonist) and their resultant utilities. Certain identified compounds will be useful in the treatment and prevention of disorders and conditions in which $PGD_2$ participates, such as, for example, allergy, asthma, and generally, inflammation conditions. Certain identified compounds will be useful in the treatment and prevention of disorders and conditions were it is advantageous to enhance the interaction of $PGD_2$ and CRTH2.

The invention provides a method for identifying a compound that modulates a CRTH2-$PGD_2$-mediated process, comprising: a) contacting CRTH2 with a test compound, in the presence of absence of $PGD_2$; and b) determining the biological effects thereof. In a typical assay, the test compound will bind, and have effects, at the same site on CRTH2 at which $PGD_2$ normally binds, although the skilled practitioner will recognize that this need not always be so, that is, the methodologies of the present invention may also be used to identify compounds acting at sites on CRTH2 remote to the $PGD_2$ binding site.

In one embodiment, the compound identified is an antagonist which interferes with the interaction of $PGD_2$ with CRTH2, or the normal result thereof. In a further embodiment, the compound identified is an agonist which mimics the normal effects of binding of $PGD_2$ on CRTH2, but at an enhanced level. In a typical embodiment, the CRTH2 activity measured is the ability to interact with $PGD_2$. In additional embodiments of the invention, the test compound is an antibody specific for CRTH2, or is an antibody specific for an epitope provided in part by $PGD_2$.

The invention further provides a method for identifying a compound that modulates a CRTH2-$PGD_2$-mediated process comprising: a) contacting a CRTH2-expressing cell with a test compound; and b) measuring the resultant level of a CRTH2 activity, or the level of expression of CRTH2 in the cell, such that if said level of measured activity or expression differs from that measured in the absence of the test compound, then a compound that modulates a CRTH2-PGD2-mediated process is identified. In one embodiment, the CRTH2 activity measured is the ability to interact with $PGD_2$. In another embodiment, the CRTH2 activity measured is the chemotactic response of the cell to $PGD_2$.

In another embodiment, this method further comprises: a) contacting a second cell which expresses CRTH2 with the identified compound; and b) determining whether the compound modulates a second CRTH2 activity. In another embodiment, either the first or the second CRTH2 activity measured is the ability to interact with $PGD_2$. In yet another embodiment, either the first or the second CRTH2 activity measured is the chemotactic response of the cell to $PGD_2$. In another embodiment, the second CRTH2 activity is the intracellular $Ca^{2+}$ concentration, the release of reactive oxygen species, or actin polymerization.

Also encompassed by the invention is a method for identifying a compound that modulates the binding of $PGD_2$ to CRTH2, comprising: (a) contacting the CRTH2 with $PGD_2$ (or an analog thereof) in the presence of a test compound; and (b) measuring the amount of $PGD_2$ (or analog) that is bound to CRTH2, such that if the amount of bound $PGD_2$ measured in (b) differs from the amount of bound $PGD_2$ measured in the absence of the test compound, then a compound that modulates the binding of $PGD_2$ to CRTH2 is identified. In one embodiment, the CRTH2 contacted in step (a) is on a cell surface. In another embodiment, the CRTH2 is immobilized to a solid surface. In another embodiment, the solid surface is a microtiter dish. In yet another embodiment, the amount of bound $PGD_2$ is measured by contacting the cell with a $PGD_2$-specific antibody.

In still another embodiment, the $PGD_2$ is labeled and the amount of bound $PGD_2$ is measured by detecting the label. In one embodiment of this method, the $PGD_2$ is labeled with a fluorescent label.

The invention further provides a method for detecting a CRTH2-$PGD_2$ related disorder in a mammal comprising measuring the either the level of CRTH2 gene expression, or of CRTH2 receptor, in a patient sample, such that if the measured level differs from the level found in clinically normal individuals, then a CRTH2-$PGD_2$ related disorder is detected.

Also encompassed by the present invention are kits. A kit is provided comprising (a) $PGD_2$ or an an analog thereof, or (b) a CRTH2 polypeptide, or (c) nucleic acid encoding a CRTH2 polypeptide or, for example, (d) a cell expressing CRTH2, as packaged in a container with appropriate instructions and additional reagents. In one embodiment, the kit further comprises instructions for use in detecting the presence of a CRTH2-$PGD_2$ related disorder in a patient.

The term "$PGD_2$-mediated" as used herein includes processes that are dependent and/or responsive, either directly or indirectly, to the level of expression, synthesis and/or activity of $PGD_2$. Such processes include, but are not limited to allergic, asthmatic, and inflammatory processes, such as chemotaxis of inflammatory cells, inhibition of platelet aggregation, relaxation and constriction of smooth muscle, and neurological regulation, including sleep, body temperature and pain response regulation.

The terms "CRTH2-$PGD_2$-related disorder" and "CRTH2-$PGD_2$-related conditions" as used herein refer to disorders and conditions in which $PGD_2$ participates, or which may be affected, beneficially or adversely, by the concentration of $PGD_2$ in a patient. Such disorders and conditions may result, for example, from an aberrant level of $PGD_2$ expression, synthesis and/or activity relative to levels found in normal, unaffected, unimpaired individuals. Such disorders include, but are not limited to, allergic disorders, asthmatic disorders, and inflammatory disorders, such as allergic rhinitis, allergic asthma, bronchoconstriction; and neurological disorders, including sleep disorders; and disorders in the regulation of body temperature or pain response.

For the purposes of the present invention, an "analog" of $PGD_2$ is a compound generally similar in structure to $PGD_2$, and which generally has the same general biological effect as $PGD_2$, at least under one condition of assay. Thus, in an assay in which the activity of potential $PGD_2$-agonist or $PGD_2$-antagonist compounds will be measured, the analog may be substituted for any $PGD_2$ itself that would otherwise be used in said assay.

B. The effects of the prostaglandins and their analogs on human eosinophil [$^3$H]-$PGD_2$ binding site.

FIG. 2 Structures of Certain $PGD_2$ Derivatives.

Figure 3A:
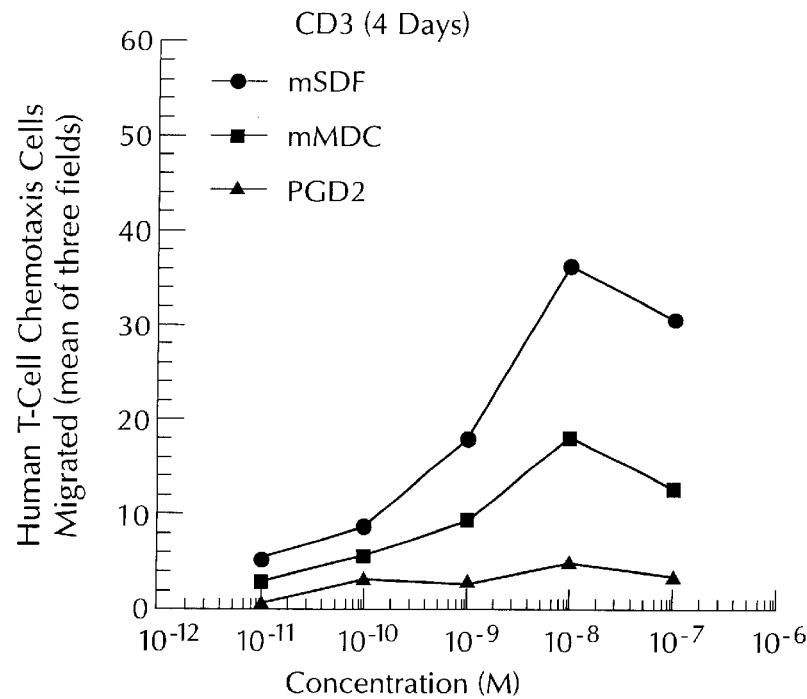

FIGS. 3A/B Chemotactic Response of $PGD_2$, mMDC and mSDF in Human T Lymphocytes.

Figure 4:
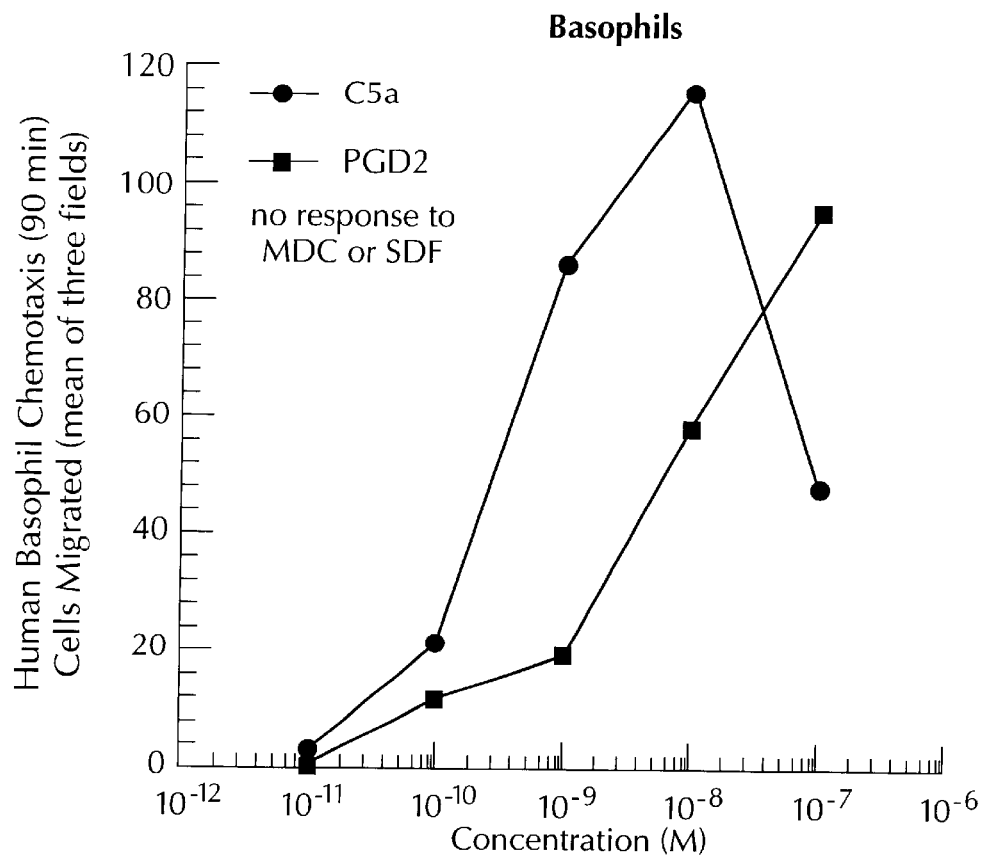

FIG. 4 Chemotactic Response of Human Basophils to $PGD_2$ and C5a.

Figure 5:
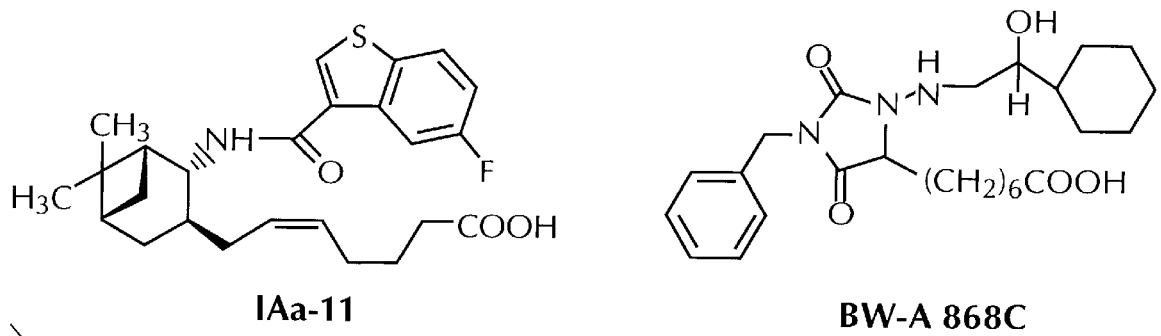

FIG. 5 Structures of $PGD_2$ Antagonists IAa-11 and BW-A 868C.

Figure 6:
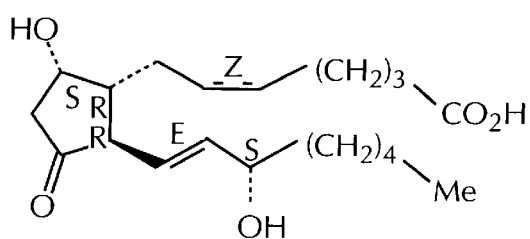
Figure 6:
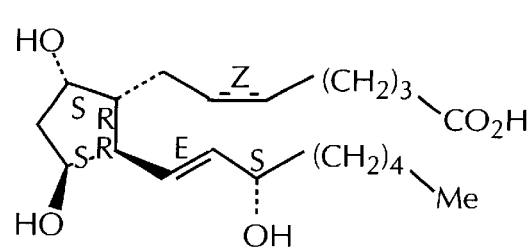
Figure 6:
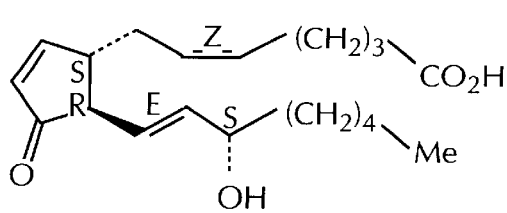
Figure 6:
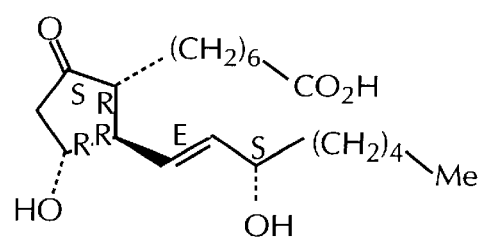
Figure 6:
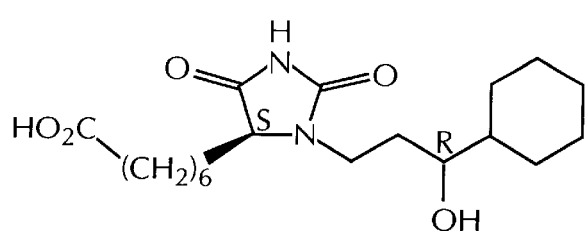
Figure 6:
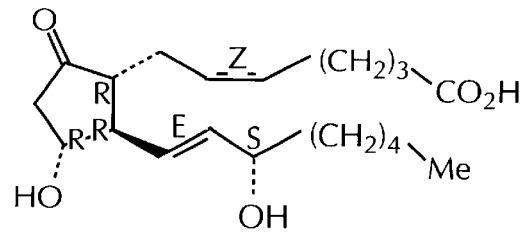
Figure 6:
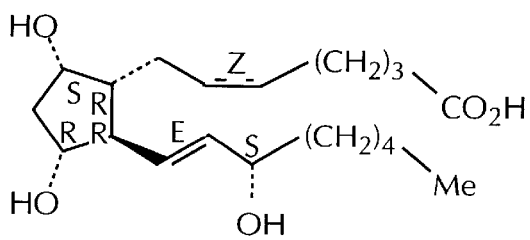
Figure 6:
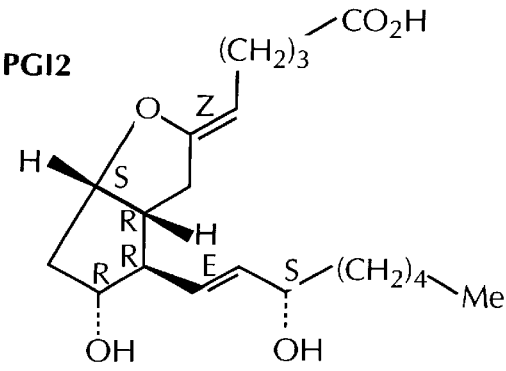

FIG. 6 Structures of prostaglandins and analogs.

Figure 7A:
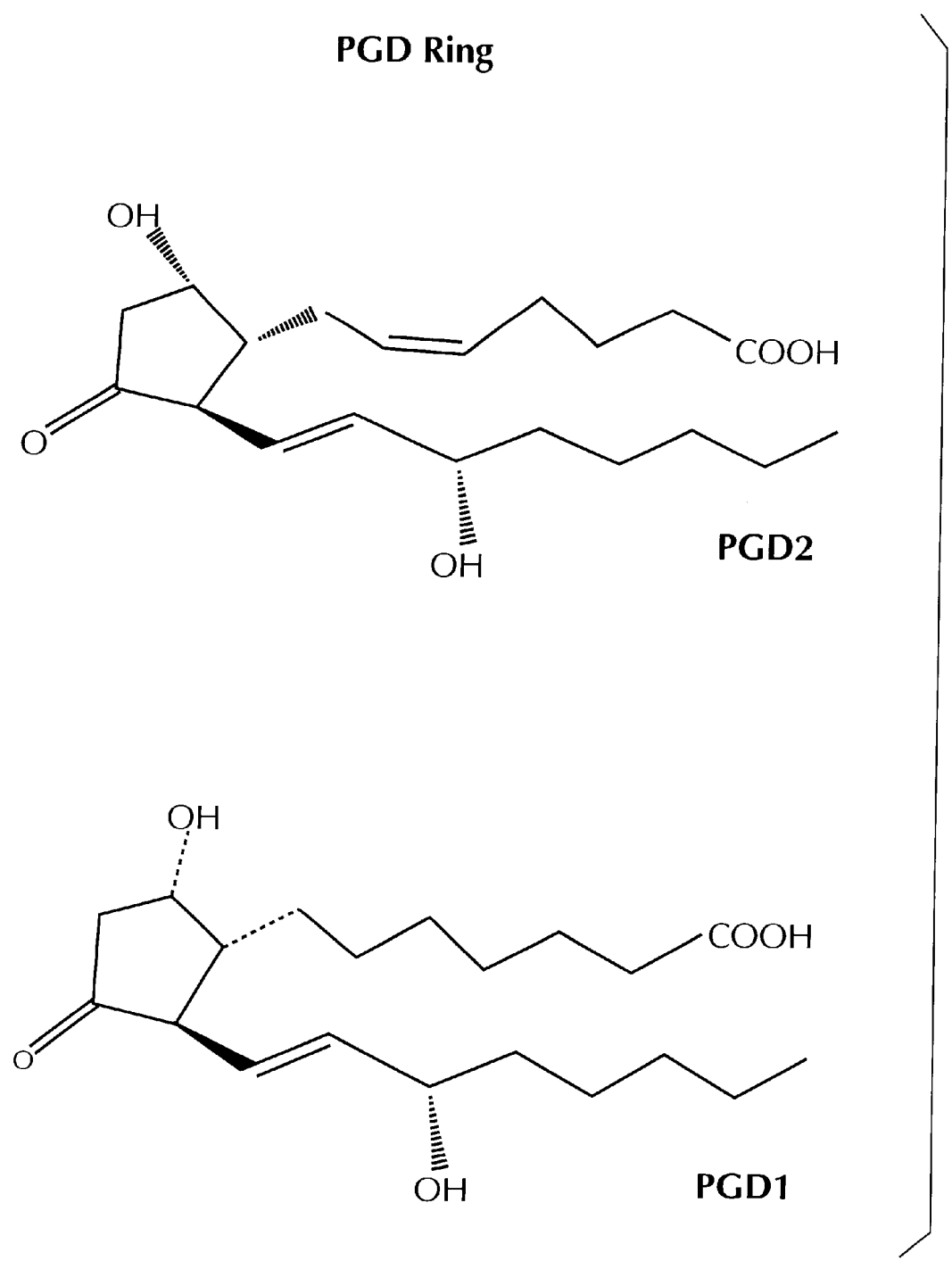
Figure 7B:
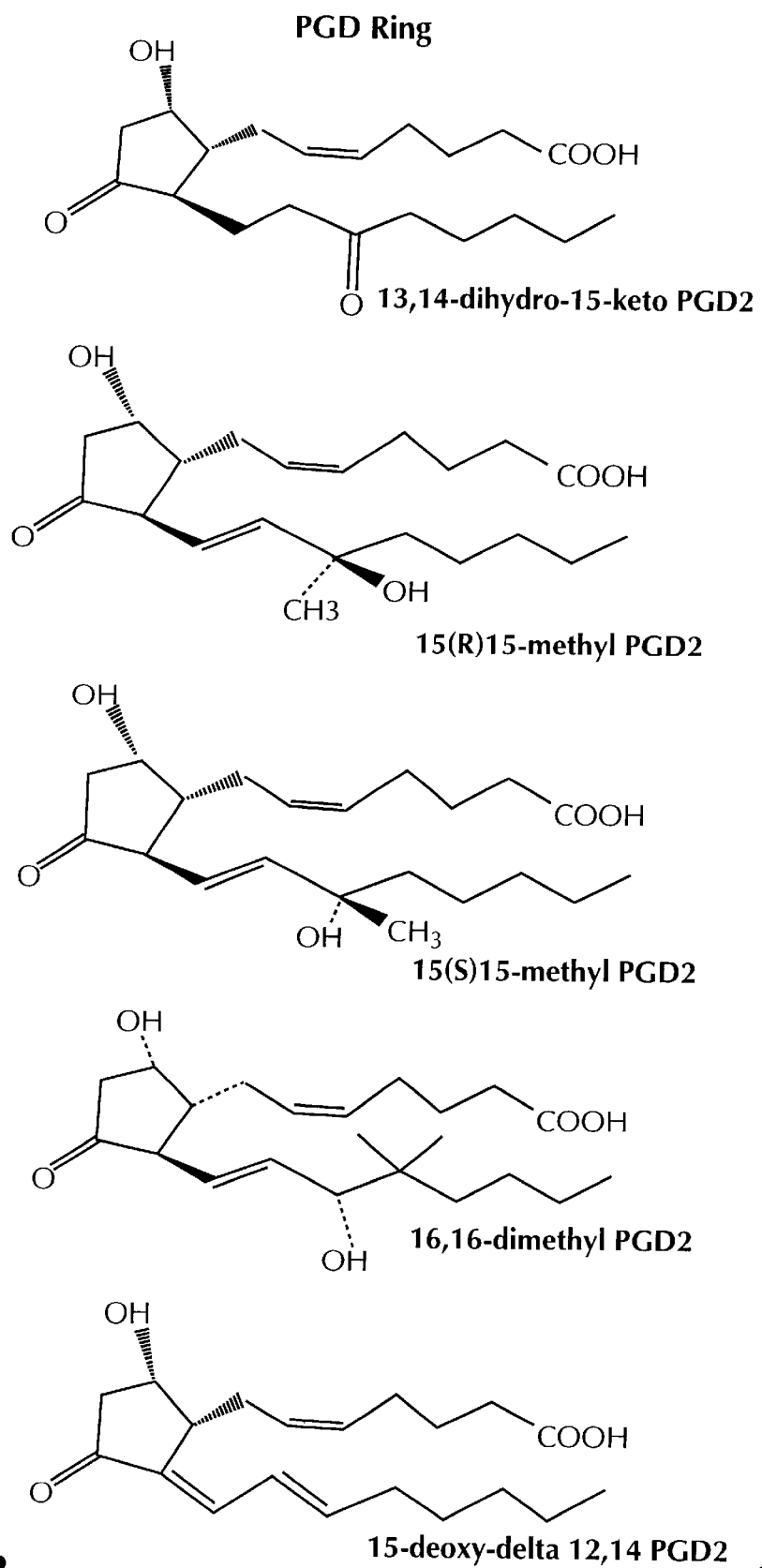

FIGS. 7A/B Structures of $PGD_2$ Agonists based on the PGD Ring.

Figure 8:
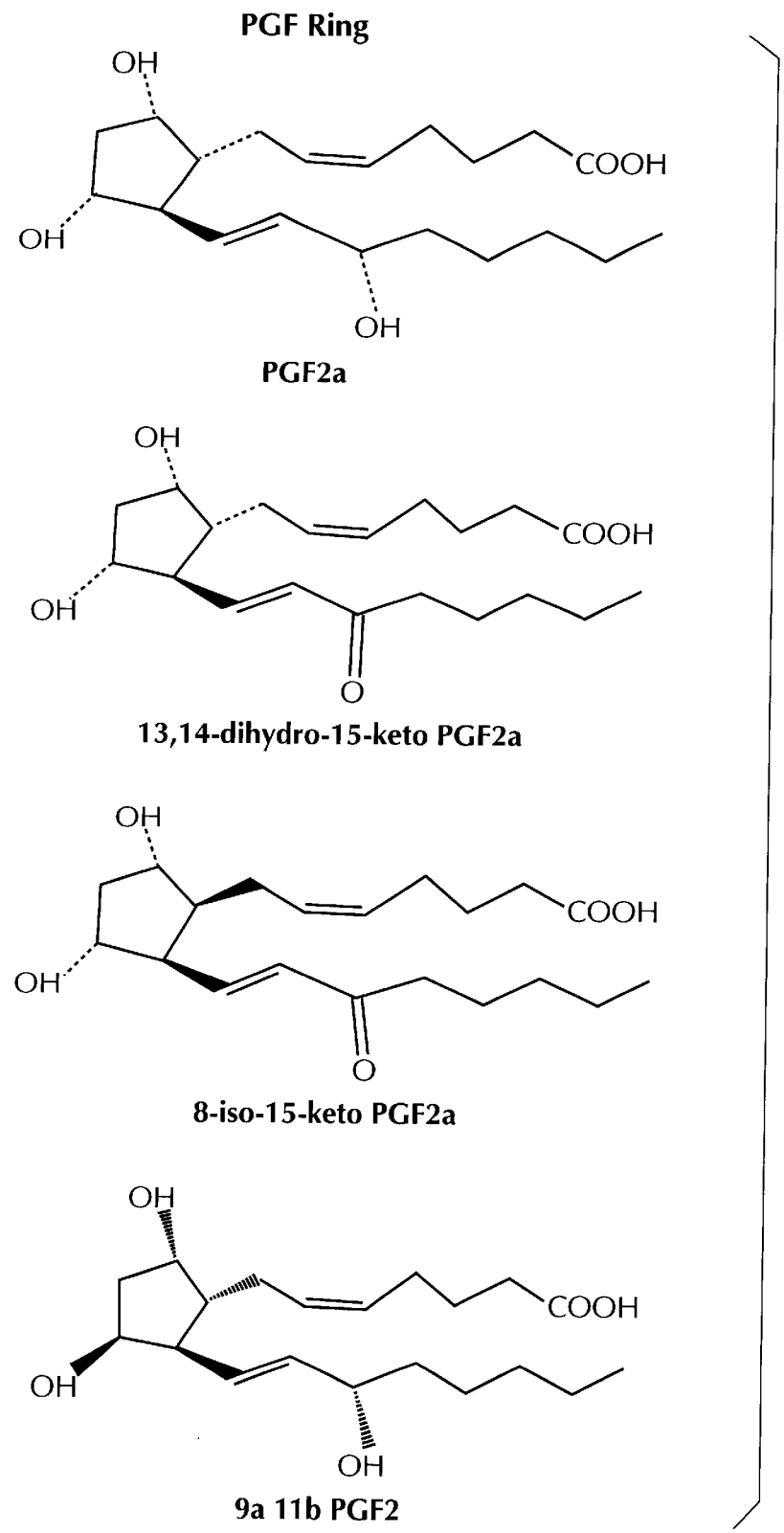

FIG. 8 Structures of $PGD_2$ Agonists based on the PGF Ring.

Figure 9:
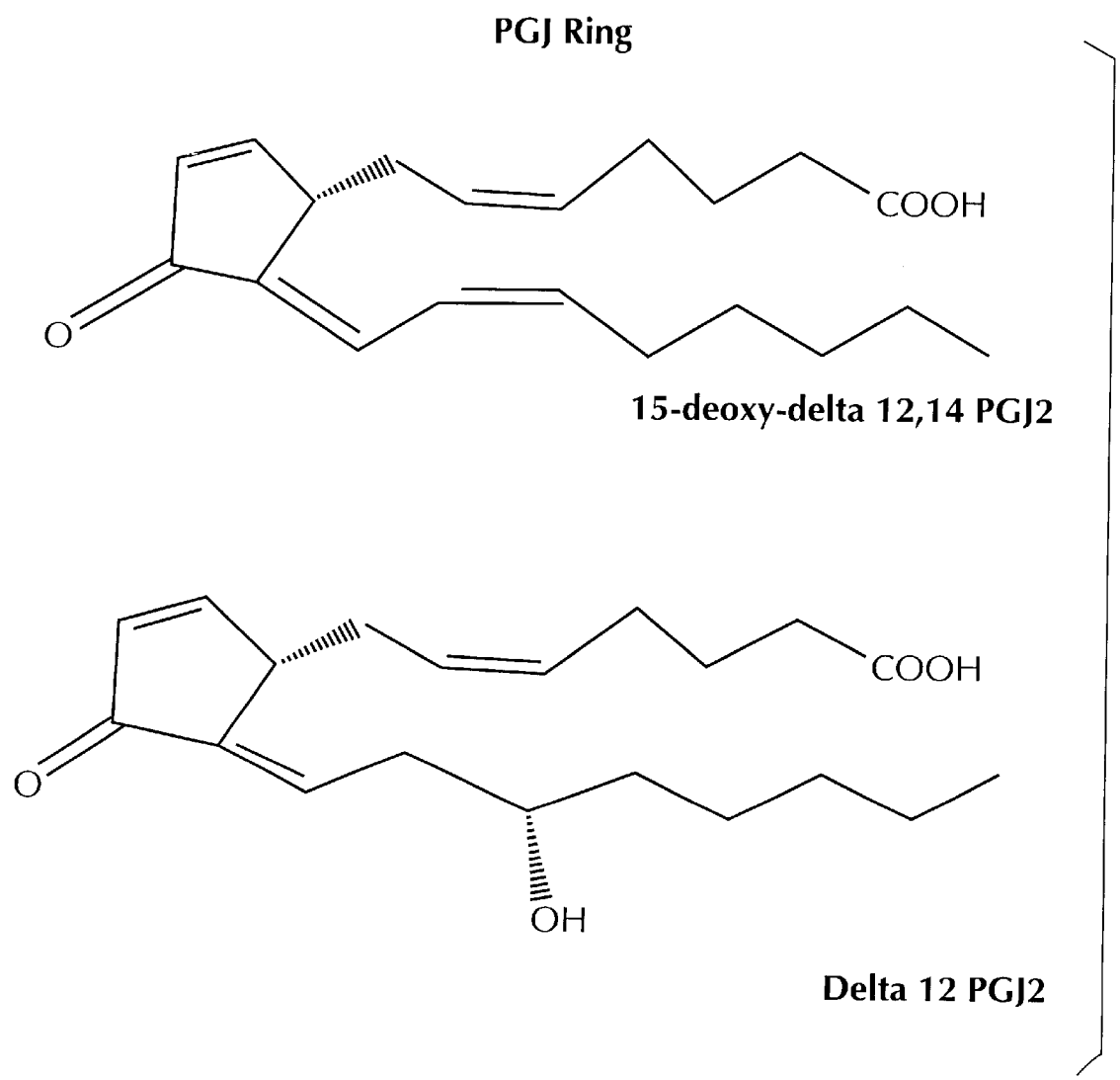

FIG. 9 Structures of $PGD_2$ Agonists based on the PGJ Ring.

Figure 10:
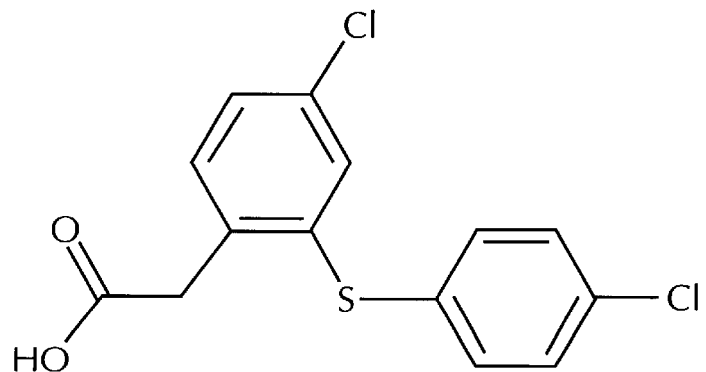
Figure 10:
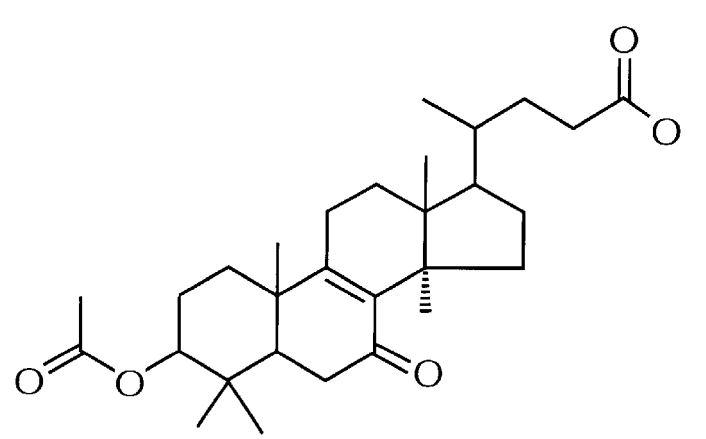
Figure 10:
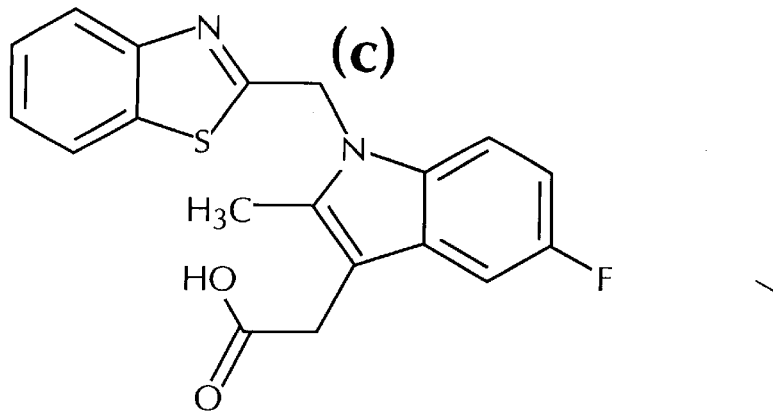
Figure 10:
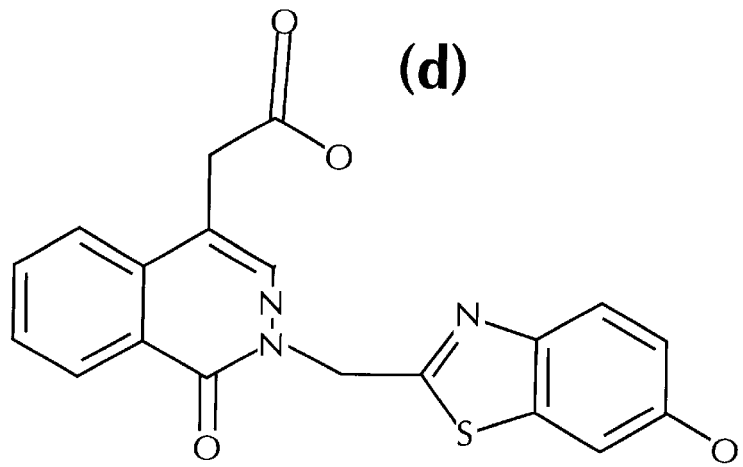

FIGS. 10 A/B Structures of Certain $PGD_2$ antagonists.

DETAILED DESCRIPTION OF THE INVENTION

Described herein are screening assays for the identification of therapeutic compounds useful for the detection and treatment of $PGD_2$-related disorders, such as allergenic disorders, asthma, and inflammatory response disorders. The assays are also adaptable for the detection of compounds that, relative to $PGD_2$ itself, show enhanced $PGD_2$-CRTH2 binding and activity. Such screening assays include first, primary screening assays, which may be adapted to high-throughput screening formats, and, second, secondary screening assays, which can be used to further characterize lead compounds identified in the primary screens. In addition, there are disclosed diagnostic and therapeutic methods for the use of identified compounds in the treatment of $PGD_2$-related disorders.

The screening assays described herein may be used to identify, for example, organic compounds, peptides and proteins (including antibodies) that modulate the interaction of $PGD_2$ with CRTH2.

Such identified compounds, and the like, may be used as agonists or antagonists of the chemotactic induction of CRTH2 by $PGD_2$. For example, compounds that affect CRTH2 activity include but are not limited to compounds that bind to CRTH2, thereby inhibiting binding of $PGD_2$, and that either block chemotactic induction (antagonists) or enhance chemotactic induction (agonists).

The methodology of the present invention is also useful to detect (or confirm the activity of) compounds that bind to $PGD_2$, thereby preventing or enhancing binding of $PGD_2$ to CRTH2. The therapeutic activity of antibodies may be confirmed according to this aspect of the invention.

Compounds that affect CRTH2 gene activity (by affecting CRTH2 gene expression, including molecules, e.g., proteins or small organic molecules, that affect transcription or interfere with splicing events so that expression of the full length or the truncated form of CRTH2 can be modulated) can also be identified in the screens of the invention.

Further, it should be noted that the assays described can also identify compounds that modulate CRTH2 signal transduction (e.g., compounds which affect downstream signaling events, such as inhibitors or enhancers of G-protein activities which may participate in transducing the signal activated by $PGD_2$, or other ligand binding to CRTH2). The identification and use of such compounds which affect signaling events downstream of CRTH2 and thus modulate effects of CRTH2 on allergic or inflammatory responses, for example, are within the scope of the invention.

The primary screening assays described herein are designed to detect compounds that modulate the $PGD_2$-CRTH2 interaction, that is, the test compounds act in the place of $PGD_2$ at the CRTH2 receptor, either negatively or positively compared with $PGD_2$, or which combine with or otherwise modify $PGD_2$, thereby affecting how it acts at the CRTH2 receptor. As described in detail below, such assays are functional assays, such as binding assays, that can be adapted to a high-throughput screening methodologies.

Binding assays can be used to identify compounds that modulate the interaction between $PGD_2$ and CRTH2. In one aspect of the invention, the screens may be designed to identify compounds that interfere with the normal interaction between CRTH2 and $PDG_2$, such as other natural prostaglandins, or analogs thereof, or other compounds. Such compounds will be useful as lead compounds for antagonists of allergenic responses, asthma and inflammatory responses. In another aspect of the invention, the screens may be designed to identify compounds that mimic the normal interaction between CRTH2 and $PDG_2$, but with enhanced effect, such as other prostaglandins, or analogs thereof, or other compounds. Such compounds will be useful as lead compounds for agonists of the CRTH2-$PDG_2$ interaction.

Binding assays may be performed either as direct binding assays or as competition binding assays. In a direct binding assay, a test compound is tested for binding either to the CRTH2 receptor, or to ligand $PGD_2$. Then, in a second step, the test compound is tested for its ability to modulate the $PGD_2$-CRTH2 interaction. Competition binding assays, on the other hand, assess the ability of a test compound to compete with $PGD_2$ for binding to CRTH2.

In a direct binding assay, either $PGD_2$ and/or CRTH2 is contacted with a test compound under conditions that allow binding of the test compound to the ligand or the receptor. The binding may take place in solution or on a solid surface. Preferably, the test compound is previously labeled for detection. Any detectable group may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound test compound. Typically, this involves washing with an appropriate buffer. Finally, the presence of a $PGD_2$-test compound complex or a CRTH2-test compound complex is detected.

In a competition binding assay, test compounds are assayed for their ability to disrupt or enhance the binding of $PGD_2$ to CRTH2. Labeled $PGD_2$ may be mixed with CRTH2 or a fragment or derivative thereof, and placed under conditions in which the interaction between them would normally occur, either with or without the addition of the test compound. The amount of labeled $PGD_2$ that binds CRTH2 may be compared to the amount bound in the presence or absence of test compound.

In a preferred embodiment, to facilitate complex formation and detection, the binding assay is carried out with one or more components immobilized on a solid surface. In various embodiments, the solid support could be, but is not restricted to, polycarbonate, polystyrene, polypropylene, polyethlene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of CRTH2, or other component, can be achieved through covalent or non-covalent attachments. In one embodiment, the attachment may be indirect, i.e. through an attached antibody. In another embodiment, CRTH2 and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using a CRTH2 which is immobilized to a solid support. Typically, the non-immobilized component of the binding reaction, in this case either $PGD_2$ or the test compound, is labeled to enable detection. A variety of labeling methods are available and may be used, such as detection of luminescent, chromophoric, fluorescent, or radioactive isotopes or groups, or detection of nonisotopic labels, such as enzymes or dyes. In one preferred embodiment, the test compound is labeled with a fluorophore such as fluorescein isothiocyanate (FITC, available from Sigma Chemicals, St. Louis).

The labeled test compounds, or $PGD_2$ plus test compounds, are then allowed to contact with the solid support, under conditions that allow specific binding to occur. After the binding reaction has taken place, unbound and non-specifically bound test compounds are separated by means of washing the surface. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and the like.

Finally, the label remaining on the solid surface may be detected by any detection method known in the art. For example, if the test compound is labeled with a fluorophore, a fluorimeter may be used to detect complexes.

In a preferred embodiment, a binding assay can be performed as follows:
(a) 300-19 cells (see below) that transiently express CRTH2 are pelleted, and washed twice at room temperature with assay buffer (Hank's balanced saline,
including $Ca^{+2}$ and $Mg^{+2}$, and supplemented with HEPES and sodium bicarbonate). The cells are resuspended at a concentration of $2\times10^7$ cells/ml. Using 96-well U-bottom microtiter dishes, the assays are set up as follows (in 150 µl volumes):
(b) 50 µl of vehicle (as 0.3% DMSO in assay buffer, total wells); or 50 µl of 30 µM cold $PGD_2$ which results in a 10 µM final assay concentration thereof [the stock solution of cold $PGD_2$ was dissolved in DMSO at a stock concentration of 10 mM, and stored at $-20°$ C., for use it was then diluted 3:1000 to final stock concentration of 30 µM];
50 µl cells ($2\times10^7$/ml for $10^6$/well);
50 µl of 6 nM [$^3$H]-$PGD_2$ is added for a final concentration of 2 nM (Amersham; 162 Ci/mmol, 0.1 Ci/ml in methanol: water: acetonitrile (3:2:1), 617 nM diluted to 10 µl per ml assay buffer for a concentration of 6 nM).
(c) The plate is allowed to incubate for 20 min at room temperature before centrifugation (2800 rpm, Sorval RT6000, 5 min, $4°$ C.). The supernatant is discarded to decrease non-specific binding. The plate (Packard Unifilter plate GF/C, previously soaked in 3% PEI for at least 1 hr) is harvested with cold assay buffer by washing 6 times with 150 µl buffer wash per well. The filterplate is dried overnight. After the addition of 50 µl scintillation fluid, the plate is counted in a scintillation counter (1 min per well). (Preferably CRTH2 is added to binding assays in the form of intact cells that express CRTH2, or as isolated cell membranes that contain CRTH2. Thus, direct binding to CRTH2, or the ability of a test compound to modulate a $PGD_2$-CRTH2 complex, may be assayed in intact cells in culture, or in animal models, in the presence and absence of the test compound).

A labeled $PGD_2$ may be mixed with cells that express CRTH2, or with crude extracts obtained from such cells, and the test compound may be added. Isolated membranes may be used to identify compounds that interact with CRTH2. For example, in a typical experiment using isolated membranes, cells may be genetically engineered to express CRTH2. Membranes can be harvested by standard techniques and used in an in vitro binding assay. Labeled ligand (e.g., $^{125}$I-labeled $PGD_2$) is bound to the membranes and assayed for specific activity; and specific binding is determined by comparison with binding assays performed in the presence of excess unlabeled (cold) ligand. Alternatively, soluble CRTH2 may be recombinantly expressed and utilized in non-cell based assays to identify compounds that bind to CRTH2. The recombinantly expressed CRTH2 polypeptide(s) or fusion proteins containing one or more of the ECDs of CRTH2 can be used in the non-cell based screening assays. Alternatively, peptides corresponding to one or more of the CDs of CRTH2, or fusion proteins containing one or more of the CDs of CRTH2, can be used in non-cell based assay systems to identify compounds that bind to the cytoplasmic portion of the CRTH2; such compounds may be useful to modulate the signal transduction pathway of the CRTH2. In non-cell based assays, the recombinantly expressed CRTH2 is attached to a solid substrate such as a test tube, microtitre well or a column, by means known to those in the art (see Ausubel et al., supra). The test compounds are then assayed for their ability to bind to the CRTH2.

Alternatively, the binding reaction may be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

In a one embodiment, for example, a phage library can be screened by passing phage from a continuous phage display library through a column containing purified CRTH2, or derivative, analog, fragment, or domain, thereof, linked to a solid phase, such as plastic beads. By altering the stringency of the washing buffer, it is possible to enrich for phage that express peptides with high affinity for CRTH2. Phage isolated from the column can be cloned and the affinities of the short peptides can be measured directly. Sequences for more than one oligonucleotide can be combined to test for even higher affinity binding to CRTH2. Knowing which amino acid sequences confer the strongest binding to CRTH2, computer models can be used to identify the molecular contacts between CRTH2 and the test compound. This will allow the design of non-protein compounds which mimic those contacts. Such a compound may have the same activity of the peptide and can be used therapeutically, having the advantage of being efficient and less costly to produce.

In another specific embodiment of this aspect of the invention, the solid support is membranes containing CRTH2 attached to a microtiter dish. Test compounds, for example, cells that express library members are cultivated under conditions that allow expression of the library members in the microtiter dish. Library members that bind to the protein (or nucleic acid or derivative) are harvested. Such methods, are described by way of example in Parmley & Smith, 1988, Gene 73:305–318; Fowlkes et al., 1992, Bio-Techniques 13:422–427; PCT Publication No. WO 94/18318; and in other references cited herein.

In another embodiment of the present invention, interactions between CRTH2 or $PGD_2$ and a test compound may be assayed in vitro. Known or unknown molecules are assayed for specific binding to CRTH2 nucleic acids, proteins, or derivatives under conditions conducive to binding, and then molecules that specifically bind to CRTH2 are identified. The two components can be measured in a variety of ways. One approach is to label one of the components with an easily detectable label, place it together with a test component(s) under conditions that allow binding to occur, perform a separation step which separates bound labeled component from unbound labeled component, and then measure the amount of bound component. In one embodiment, CRTH2 can be labeled and added to a test agent, using conditions that allow binding to occur. Binding of the test agent can be determined using polyacrylamide gel analysis to compare complexes formed in the presence and absence of the test agent.

In yet another embodiment, binding of $PGD_2$ to CRTH2 may be assayed in intact cells in animal models. A labeled $PGD_2$ may be administered directly to an animal, with and without a test compound. The uptake of $PGD_2$ may be measured in the presence and the absence of test compound. For these assays, host cells to which the test compound has been added may be genetically engineered to express the CRTH2 and/or $PGD_2$, which may be transient, induced or constitutive, or stable. For the purposes of the screening methods of the present invention, a wide variety of host cells may be used including, but not limited to, tissue culture cells, mammalian cells, yeast cells, and bacteria. Each cell type has its own set of advantages. Mammalian cells such as T cells or other cells that express CRTH2, i.e. brain, thymus, muscle, spleen, skin and other tissues, may be a preferred cell type in which to carry out the assays of the present invention. Bacteria and yeast are relatively easy to cultivate but process proteins differently than mammalian cells.

In some cases, a functional CRTH2 ligand may not form a thermodynamically stable complex with CRTH2, and would therefore not be detectable by primary assays which require the formation of stable binary complex. Such ligands, however, may be detectable by kinetic measurements of complex formation. It is known, for example, that $PGD_2$ binding to CRTH2 and to DP is differentially regulated by temperature and the presence of $Ca^{2+}$ and $Mg^{2+}$ ions. Such methods include, for example, kinetic measurement of on rates and off rates of ligand binding to the receptor. Thus, binding assays of the invention also include kinetic studies and measurements.

In addition, in some instances, responses of G protein-coupled receptors have been observed to subside, or become desensitized with prolonged exposure to ligand. In a further embodiment of the invention, assays may be utilized to identify compounds that block the desensitization of the CRTH2 receptor, and such compounds may be used to sustain the activity of CRTH2. Such compounds can be used as part of a therapeutic method for the treatment of $PGD_2$-related disorders, such as allergenic and inflammatory response disorders, such as asthma.

In one embodiment of the invention, for example, an assay which is less dependent upon the formation of thermodynamically stable complexes is a scintillation proximity assay (described in U.S. Pat. No. 4,568,649). Purified or partially purified CRTH2 or CRTH2 membranes are coated onto the surface of a scintillant-loaded solid phase (e.g., beads) and the solid phase is treated with a blocking agent such as albumin or serum. Radiolabeled test compounds (e.g., $^{33}$P-labeled) are then mixed with the CRTH2-coated beads, under conditions that would allow specific binding of a candidate specific binding test compound to the CRTH2 on the solid phase. After washing to remove excess or non-specific binding, if specific binding of a labeled test compound and CRTH2 took place, the radiolabel is brought into close proximity to the scintillant, allowing the scintillant to emit light, which is detectable with a scintillation counter.

In an alternative embodiment, an affinity capture scintillation proximity assay may be used so that binding may be performed in solution. In this assay, CRTH2 is purified and labeled with an affinity label, such as biotin. Biotinylated CRTH2 is then mixed with the radiolabeled test compound, under conditions that allow solution binding to occur. Biotinylated CRTH2 including complexes of CRTH2 and test compound are captured on streptavidin-coated scintillant-loaded beads (available from Amersham) and counted in a scintillation counter, as described above.

Chemotaxis assays may also be used as primary assays. One biological effect of the interaction between a prostaglandin receptor of type CRTH2 and an attractant is the induction of the directional migration of cells expressing the receptor toward the particular attractant, a process known as chemotaxis. A chemotaxis assay, as described herein, may be used to screen compounds that interfere with the interaction of the CRTH2 receptor and the attractant $PGD_2$. Such chemotaxis assays are adaptable to high throughput screening methods, and can thus be used in as a primary assay to identify CRTH2 antagonists. A number of techniques have been developed to assay chemotactic migration (see, e.g., Leonard et al., 1995, "Measurement of α and β Chemokines", in Current Protocols in Immunology, 6.12.1–6.12.28, Ed. Coligan et al., John Wiley & Sons, Inc. 1995).

In one embodiment, for example, a compound can be tested for its ability to modulate the ability of $PGD_2$ to induce migration of cells that express CRTH2 using a chemoattractant gradient in a multiwell Boyden chemotaxis chamber. This apparatus typically contains a chamber bottom with 48 U-bottom wells, into which is placed the chemoattractant, or compound to be tested for chemoattractant activity. A polycarbonate membrane covered with a sealing gasket separates the bottom chamber from the 48-holed chamber top, into which a cell suspension is added to the wells formed by the membrane and the chamber top.

In a specific example of this method, a competitive assay is performed to test compounds for their ability to interrupt the attraction of CRTH2 cells to $PGD_2$. In this method, test compounds are diluted into the bottom wells of the Boyden chemotaxis chamber. A constant amount of $PGD_2$ is also added to this dilution series, at a concentration known to have a chemotactic effect on CRTH2 cells. As a control, at least one aliquot contains only $PGD_2$. Cells expressing CRTH2 are resuspended at $3-3.5\times10^6$ cells/ml in RPMI 1640 supplemented with 10 mM HEPES and 1 mg/ml bovine serum albumin (Sigma, St. Louis, Mo.), and placed into the upper wells of the chamber. The chambers are incubated for 90–120 minutes at 37° C. in a humidified $CO_2$ incubator. After the incubation period, the number of migrating cells on the lower surface of the membrane filter is counted using light microscopy. The contribution of the test compound to the chemotactic activity of $PGD_2$ is measured by comparing the chemotactic activity of the aliquots containing only $PGD_2$ with the activity of aliquots containing test compound and $PGD_2$. If addition of the test compound to the $PGD_2$ solution results in a decrease in the number of cells detected on the lower surface of the membrane relative to the number of cells detected using a solution containing only $PGD_2$, then there is identified an antagonist of $PGD_2$ induction of chemotactic activity of cells expressing CRTH2. In contrast, if the addition of the test compound to the $PGD_2$ solution results in a decrease in the number of cells detected on the lower surface of the membrane (relative to the number of cells detected using a solution containing only $PGD_2$), then an agonist of $PGD_2$ induction of chemotactic activity of cells expressing CRTH2 is identified.

The methods of the invention can routinely be performed in a high-throughput fashion for rapidly screening multiple test compounds. In particular, the cell systems used in such methods can be expressed and assayed in any multiple copy format known to those of skill in the art, including, but not limited to microtiter plates, spotting on agar plates, agar wells, spotting on chips and the like. Likewise, standard multiple manipulation techniques including but not limited to robotic handling techniques, can be utilized for multiple deposition of cells and/or test compounds.

After identification of a test compound that modulates the interaction of $PGD_2$ with CRTH2, secondary screening assays may be used to further characterize the test compound for its effect on the biological activity of $PGD_2$, CRTH2, and $PGD_2$-CRTH2 signaling pathways. Various assays can be adapted to use as a secondary screen. For example, such methods include, but are not limited to, binding assays, chemotaxis assays, adhesion assays, intracellular calcium mobilization assays, oxygen release assays, and actin polymerization assays. Examples of such assays are discussed in detail hereinbelow.

Binding assays may be performed as a secondary assay, instead of, or in addition to a primary binding assays. In one embodiment, where a direct binding assay was used as a primary screen, a competition assay may be used as a secondary screen. In another embodiment, a binding assay may be used for a compound identified by a functional primary screen, such as a high-throughput chemotaxis screening assay. In another embodiment, a compound identified in a primary screen using a binding assay may be further analyzed in a secondary screen using a second type of binding assay. For example, a compound identified using a CRTH2 affinity column assay, may be tested in a secondary screen by kinetic analysis of its binding interaction.

The chemotaxis assay may be used as a secondary assay. A test compound identified by the primary screening assay to interfere with the binding of $PGD_2$ to CRTH2, or, alternatively, to enhance the binding of $PGD_2$ to CRTH2, can be tested for biological activity using a chemotaxis assay. As described above, chemokines can induce directional migration of cells via their interaction with a cell-type specific chemokine receptor, and a number of techniques have been developed to test this chemotactic migration (see, e.g., Leonard et al., 1995, "Measurement of α and β Chemokines", in Current Protocols in Immunology, 6.12.1–6.12.28, Ed. Coligan et al., John Wiley & Sons, Inc. 1995). Thus, in one embodiment, for example, a compound can be tested for its ability to modulate the ability of $PGD_2$ to induce migration of cells that express CRTH2 using a chemokine gradient in a multiwell Boyden chemotaxis chamber.

In a specific example of this method, a serial dilution of a $PGD_2$/CRTH2 antagonist or agonist test compound identified in the primary screen is placed in the bottom wells of the Boyden chemotaxis chamber. A constant amount of $PGD_2$ is also added to this dilution series. As a control, at least one aliquot contains only $PGD_2$. The method and the assay conditions are as described in the primary screening assay, and the number of migrating cells on the lower surface of the membrane filter is counted using light microscopy. The contribution of the antagonist or agonist compound to the chemotactic activity of $PGD_2$ is measured by comparing the chemotactic activity of the aliquots containing only $PGD_2$ with the activity of aliquots containing test compound and $PGD_2$. If addition of the test compound to the $PGD_2$ solution results in a decrease in the number of cells detected on the lower surface of the membrane relative to the number of cells detected using a solution containing only PGD2, then an antagonist of $PGD_2$ induction of chemotactic activity of cells expressing CRTH2 is identified. In contrast, if the addition of the test compound to the $PGD_2$ solution results in a decrease in the number of cells detected on the lower surface of the membrane relative to the number of cells detected using a solution containing only $PGD_2$, then an agonist of $PGD_2$ induction of chemotactic activity of cells expressing CRTH2 is identified.

Another secondary assay is the reactive oxygen species release assay. One measure of $PGD_2$-induced activation of CRTH2 cells, such as eosinophils, is the intracellular release of reactive oxygen species. This can be tested in a reactive oxygen species release assay, or ROS, using lucigenin-dependent chemiluminescence to measure reactive oxygen species release. In this method, freshly isolated eosinophils are prepared, by standard methods, and resuspended at concentration $2-4\times10^6$ cells/ml in (RPMI; 10 mM HEPES; 1× Pen/Strep; 0.5% FBS) at room temperature. Immediately prior to use, 1 ml of cell suspension is added to 9 ml of buffer, prewarmed to 37° C. for 15 minutes, and added 0.5 ml of 200 mM Lucigenin.

Test compounds (made as 10,000× DMSO stocks) are diluted in buffer with DMSO (1.5 ul of DMSO/2.5 ml Buffer) and 25 µl/well added to white 96-well culture plate and placed in a 37° C. incubator. Isolated cells (held at room temperature) are diluted with room temperature buffer to 2–4×106 cells/ml, and incubated in a water bath at 37° C. for 15 minutes. At 15 minutes, 0.5 ml 200 mM lucigenin (bis-N-Methylacridinium Nitrate; Sigma, St. Louis, Mo.) is added to 10 ml of the cell suspension, mixed, and 100 µl/well is added to the prewarmed microtiter plate. The plate is returned to 37° C. for 5 minutes, at which time 25 µl of stimulus is added) The plate is read in the luminometer for 8 cycles. The luminescence of test compounds can be tested in the presence of $PGD_2$, relative to a control sample containing $PGD_2$ alone. A compound that interferes with the ability of $PGD_2$ to result in intracellular reactive oxygen species release in CRTH2 cells, is a candidate for a CRTH2 antagonist.

Another secondary screening assay is the calcium mobilization assay. Elevation in intracellular ionized calcium concentration ($[Ca^{2+}]_i$) is an early indicator of chemotactic activation. Indeed, in calcium flux studies described below, it is demonstrated that even low levels of PGD2 increase $[Ca^{2+}]_i$ mobilization in cells that express CRTH2. Such calcium flux assays can be used as secondary screens to further characterize modulators of $PGD_2$/CRTH2 interactions. Intracellular calcium ion concentrations can be measured in cells that express CRTH2 in the presence of $PGD_2$, and/or in the presence and the absence of a test compound.

Calcium mobilization can be detected and measured by flow cytometry, and by labeling with fluorescent dyes that are trapped intracellularly. For example, the dye Indo-1 exhibits a change in emission spectrum upon binding calcium. The ratio of fluorescence produced by the calcium-bound dye to that produce by the unbound dye is used to estimate the intracellular calcium concentration. In one embodiment, for example, the following method can be used. Cells that express CRTH2 are collected, and resuspended in fresh media at ~2×10⁵/ml the day before performing the calcium flux assay. Cells are incubated at 37° C. for not longer than 20–30 minutes, and then spun down and resuspended in 50 ml fresh PTI buffer (Hank's Buffer, pH 7.2–7.4; 10 mM Hepes; 1.6 mM $CaCl_2$) containing Indo-1 AM, pre-warmed to 37° C., at a concentration of 10 million per ml. Cells are excited, and fluorescence is measured using a fluorimeter (Photon Technology Corporation, International). After the readout has stabilized, the time axis is reset, and $PGD_2$ is added at a specific time point (e.g., 20 seconds). After response, the following reagents are added to the cuvette, to release and chelate total calcium, in the following order: 20 µl of 18% Triton X-100, 20 µl of 3M Tris, pH 8.5, and 20 µl of 0.5 M EGTA, pH 8.5. The experiment is repeated in the presence and the absence of a test compound. In the absence of test compound, $PGD_2$ results in increased ($[Ca^{2+}]_i$) in cells that express CRTH2, with an $EC_{50}$ of 15 nM. Therefore, in the presence of an agonist test compound, the $EC_{50}$ would be expected to be higher than this value, whereas in the presence of an agonist test compound, the $EC_{50}$ would be expected to decrease.

Yet another secondary screening assay is an actin polymerization assay. Another biological effect of the interaction of $PGD_2$ with CRTH2 is actin polymerization. Thus, an actin polymerization assay may be used as a secondary screen to characterize the activity of a compound isolated in the primary screening assays of the invention. In one embodiment, actin polymerization may be assayed using an actin-specific fluorescent label, nitrobenzoxadiazole (NBD)-phallacidin, which binds polymerized actin fiber. In a specific embodiment, the assay may be performed as follows: cell preparations are resuspended at 5–10×10⁶ cells/ml in RPMI 1640 plus 10 mM HEPES, 100/10 Pen/Strep, and 0.5% FCS. The cell suspension is aliquoted (100 µL per well) into a 96-well U-bottom polypropylene microtiter plate. 50 ul of the appropriate stimulus ($PGD_2$ or test compound, or both $PGD_2$ and test compound) is added using an 8-channel pipette followed exactly 25 seconds later by 50 ul of a stopping solution which contains lysophosphotidyl-choline (0.5 mg/ml), Hank's balanced salt solution (100 ul 10×), 16% formaldehyde (800 ul), and 6.6 uM NBD-phallacidin in MEOH (100 ul). The plate is allowed to sit at room temperature for 15 minutes. The plate is then centrifuged at 1000 rpm for 5 minutes, the supernatants flicked off and the cell pellets resuspended in 250 ul PBS plus 2%FCS and 0.2% sodium azide. Each sample is then read on a FACS Caliber instrument. Cells are gated using the forward scatter/side scatter data in the lymphocyte area. Responses are measured by the change in median FL-1 fluorescence between vehicle treated cells and stimulus treated cells. Test compounds can be assayed in the presence and absence of PGD2, and compared to a sample containing $PGD_2$ alone. A compound that reduces $PGD_2$-induced actin polymerization of CRTH2 cells is identified as a candidated CRTH2 antagonist.

The screening assays described herein may be used to identify organic compounds, or peptides or proteins, for example, that modulate the interaction of the $PGD_2$ with CRTH2. The substances which may be screened in accordance with the invention therefore also include antibodies and fragments thereof. Peptidomimetic organic compounds that bind, for example, to the extra-cellular domain (ECD) of CRTH2 and either inhibit the activity triggered by the natural ligand (i.e., antagonists) or mimic the activity triggered by the natural ligand (i.e., agonists), may also be screened. Additionally, organic compounds, peptides, antibodies or fragments thereof, to which the ECD (or a portion thereof) of CRTH2 is covalently attached may also bind to and therefore "neutralize" PGD2, otherwise the natural CRTH2 ligand. Screening of such complex reagents is also within the practice of the invention.

Compounds that may be used for screening include, but are not limited to, peptides such as, for example, soluble peptides, including but not limited to members of random peptide libraries; (see, e.g., Lam et al., 1991, Nature 354:82–84; Houghten et al., 1991, Nature 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang et al., 1993, Cell 72:767–778), antibodies (including, but not limited to, polyclonal, monoclonal, humanized, anti-idiotypic, chimeric or single chain antibodies, and FAb, F(ab')₂ and FAb expression library fragments, and epitope-binding fragments thereof), and small organic or inorganic molecules.

In one embodiment of the present invention, peptide libraries may be used as a source of test compounds that can be used to screen for modulators of HSPR interactions. Diversity libraries, such as random or combinatorial peptide or nonpeptide libraries can be screened for molecules that specifically bind to the HSP receptor. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott & Smith, 1990, Science 249–386–390; Devlin et al., 1990, Science, 249:404–406; Christian, et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley & Smith, 1989, Adv. Exp. Med. Biol. 251:215–218; Scott & Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar & Pabo, 1993, Science 263:671–673; and PCT Publication No. WO 94/18318.

In another embodiment of the present invention, the screening may be performed by adding the labeled $PGD_2$ to in vitro translation systems such as a rabbit reticulocyte lysate (RRL) system and then proceeding with in vitro priming reaction. in vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

Compounds that can be tested and identified methods described herein can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal, plant or animal extracts.

Furthermore, diversity libraries of test compounds, including small molecule test compounds, may be utilized. For example, libraries may be commercially obtained from Specs and BioSpecs B.V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), and Asinex (Moscow, Russia).

Still further, combinatorial library methods known in the art, can be utilize, including, but not limited to: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145). Combinatorial libraries of test compounds, including small molecule test compounds, can be utilized, and may, for example, be generated as disclosed in Eichler & Houghten, 1995, Mol. Med. Today 1:174–180; Dolle, 1997, Mol. Divers. 2:223–236; and Lam, 1997, Anticancer Drug Des. 12:145–167.

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994. J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Bio/Technques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223, 409), plasmids (Cull et al., 1992, Proc. Natl. Acad. Sci. USA 89:1865–1869) or phage (Scott and Smith, 1990, Science 249:386–390; Devin, 1990, Science 249:404–406; Cwirla et al., 1990, Proc. Natl. Acad. Sci. USA 87:6378–6382; and Felici, 1991, J. Mol. Biol. 222:301–310).

Screening the libraries can be accomplished by any of a variety of commonly known methods. See, e.g., the following references, which disclose screening of peptide libraries: Parmley & Smith, 1989, Adv. Exp. Med. Biol. 251:215–218; Scott & Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al., Rebar & Pabo, 1993, Science 263:671–673; and PCT Publication No. WO 94/18318.

Among the test compounds that can be tested are compounds, including small organic molecule compounds that are know in the art to act as prostaglandin inhibitors.

Upon identification of a compound that modulates the interaction of $PGD_2$ with CRTH2, such a compound can be further investigated to test for an ability to alter the allergenic or inflammatory response. In particular, for example, the compounds identified via the present methods can be further tested in vivo in accepted animal models of $PDG_2$-related disorders, such as, e.g., allergy, asthma, and inflammation.

Computer modeling and searching technologies permit identification of compounds, or the improvement of already identified compounds, that can modulate the interaction of $PGD_2$ with CRTH2. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site (typcially a binding site) is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active (binding) site, either experimentally, by modeling, or by a combination, candidate modulating compounds can be identified by searching databases containing compounds along with information on their molecular structure. Such a search seeks compounds having structures that match the determined active (binding) site structure and that interact with the groups defining the active site. Such a search can be manual, but is preferably computer assisted. These compounds found from this search are potential CRTH2-modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active (binding) site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active (binding) sites of either CRTH2 or $PGD_2$, and related prostaglandins and their analogs, will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al.,) 1988, Acta Pharmaceutical Fennica 97:159–166); Ripka (1988 New Scientist 54–57); McKinaly and Rossmann (1989, Annu. Rev. Pharmacol. Toxiciol. 29:111–122); Perry and Davies, OSAR: Quantitative Structure-Activity Relationships in Drug Design pp. 189–193 Alan R. Liss, Inc. 1989; Lewis and Dean (1989, Proc. R. Soc. Lond. 236:125–140 and 141–162); and, with respect to a model receptor for nucleic acid components, Askew, et al,. (1989, J. Am. Chem. Soc. 111:1082–1090). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

CRTH2 protein, polypeptides and peptide fragments, mutated, truncated or deleted forms of the CRTH2 and/or CRTH2 fusion proteins can be prepared for a variety of uses, including but not limited to the generation of antibodies, as reagents in diagnostic assays, the identification of other cellular gene products involved in the regulation of $PGD_2$-related disorders, as reagents in assays for screening for compounds that can be used as pharmaceutical reagents in the treatment of $PGD_2$-related disorders. Additionally, based upon information gained from interacting CRTH2 and $PGD_2$, peptide fragments of CRTH2 can be derived which inhibit the normal binding of circulating $PGD_2$ to CRTH2 receptors molecules, for in vivo therapeutic use.

CRTH2 peptides, polypeptides, and fusion proteins can be prepared by recombinant DNA techniques. For example, nucleotide sequences encoding one or more of the four domains of the ECD of the serpentine CRTH2 can be synthesized or cloned and ligated together to encode a soluble ECD of the CRTH2. The DNA sequence encoding one or more of the four ECDs can be ligated together directly or via a linker oligonucleotide that encodes a peptide spacer. Such linkers may encode flexible, glycine-rich amino acid sequences thereby allowing the domains that are strung together to assume a conformation that can bind CRTH2 ligands. Alternatively, nucleotide sequences encoding individual domains within the ECD can be used to express CRTH2 peptides.

A variety of host-expression vector systems may be utilized to express nucleotide sequences encoding the appropriate regions of CRTH2 to produce such polypeptides. Where the resulting peptide or polypeptide is a soluble derivative (e.g., peptides corresponding to the ECDs; truncated or deleted in which the TMs and/or CDs are deleted) the peptide or polypeptide can be recovered from the culture media. Where the polypeptide or protein is not secreted, the CRTH2 product can be recovered from the host cell itself.

The host-expression vector systems also encompass engineered host cells that express CRTH2 or functional equivalents in situ, i.e., anchored in the cell membrane. Purification or enrichment of CRTH2 from such expression systems can be accomplished using appropriate detergents and lipid micelles and methods well known to those skilled in the art. However, such engineered host cells themselves may be used in situations where it is important not only to retain the structural and functional characteristics of CRTH2, but to assess biological activity, e.g., in drug screening assays.

The host-expression vector systems that may be used for purposes of the invention include but are not limited to microorganisms such as bacteria (e.g., E. coli, B. subtilis) transformed with recombinant bacteriophage DNA, plasmid DNA or cosmid DNA expression vectors containing CRTH2 nucleotide sequences; yeast (e.g., Saccharomyces, Pichia) transformed with recombinant yeast expression vectors containing CRTH2 nucleotide sequences; insect cell systems infected with recombinant virus expression vectors (e.g., baculovirus) containing CRTH2 sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CRTH2 nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the CRTH2 gene product being expressed. For example, when a large quantity of such a protein is to be produced, for the generation of pharmaceutical compositions of CRTH2 protein or for raising antibodies to the CRTH2 protein, for example, vectors which direct the expression of high levels of fusion protein products that are readily purified may be desirable. Such vectors include, but are not limited, to the E, coli expression vector pUR278 (Ruther et al., 1983, EMBO J. 2:1791), in which the CRTH2 coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509), and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$•nitriloacetic acid-agarose columns and histidine-tagged proteins are selectively eluted with imidazole-containing buffers.

In an insect system, *Autographa californica* nuclear polyhedrosis virus (AcNPV) is used as a vector to express foreign genes. The virus grows in *Spodoptera frugiperda* cells. The CRTH2 coding sequence may be cloned individually into non-essential regions (for example the polyhedrin gene) of the virus and placed under control of an AcNPV promoter (for example the polyhedrin promoter). Successful insertion of a CRTH2 gene coding sequence will result in inactivation of the polyhedrin gene and production of non-occluded recombinant virus (i.e., virus lacking the proteinaceous coat coded for by the polyhedrin gene). The recombinant viruses are then used to infect cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the CRTH2 nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the CRTH2 gene product in infected hosts (see, e.g., Logan & Shenk, 1984, Proc. Natl. Acad. Sci. USA 81:3655–3659). Specific initiation signals may also be required for efficient translation of inserted CRTH2 nucleotide sequences. These signals include the ATG initiation codon and adjacent sequences. In cases where an entire CRTH2 gene or cDNA, including its own initiation codon and adjacent sequences, is inserted into the appropriate expression vector, no additional translational control signals may be needed. However, in cases where only a portion of the CRTH2E coding sequence is inserted, exogenous translational control signals, including, perhaps, the ATG initiation codon, must be provided. Furthermore, the initiation codon must be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. Accordingly, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3 and WI38 cell lines.

For long-term, high-yield production of recombinant proteins, stable expression is preferred. For example, cell lines which stably express the CRTH2 sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the CRTH2 gene product. Such engineered cell lines may be particularly useful in screening and evaluation of compounds that affect the endogenous activity of the CRTH2 gene product.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Antibodies that specifically recognize one or more epitopes of CRTH2, or epitopes of conserved variants of CRTH2, or peptide fragments of CRTH2 are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of CRTH2 in a biological sample and may, therefore, be utilized as part of a diagnostic or prognostic technique whereby patients may be tested for abnormal amounts of CRTH2. Antibodies that specifically recognize mutant forms of CRTH2, may be particularly useful as part of a diagnostic or prognostic technique. Such antibodies may also be utilized in conjunction with, for example, compound screening schemes, as described, above, for the evaluation of the effect of test compounds on expression and/or activity of the CRTH2 gene product. Additionally, such antibodies can be used in conjunction with the gene therapy techniques described, below, e.g., to evaluate the normal and/or engineered CRTH2-expressing cells prior to their introduction into the patient. Such antibodies may additionally be used as a method for the inhibition of abnormal CRTH2 activity. Thus, such antibodies may, therefore, be utilized as part of PGD$_2$-related disorder treatment methods.

For the production of antibodies, various host animals may be immunized by injection with CRTH2, a CRTH2 peptide (e.g., one corresponding the a functional domain of the receptor, such as ECD, TM or CD), truncated CRTH2 polypeptides (CRTH2 in which one or more domains, e.g., the TM or CD, has been deleted), functional equivalents of CRTH2 or mutants of CRTH2. Such host animals may include but are not limited to rabbits, mice, hamsters and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497 and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against CRTH2 gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to CRTH2 can, in turn, be utilized to generate anti-idiotype antibodies that "mimic" CRTH2, using techniques well known to those skilled in the art (see, e.g., Greenspan & Bona, 1993, FASEB J 7(5):437–444; and Nissinoff, 1991, J. Immunol. 147(8):2429–2438). For example antibodies which bind to the CRTH2 ECD and competitively inhibit the binding of melanocortins to the CRTH2 can be used to generate anti-idiotypes that "mimic" the ECD and, therefore, bind and neutralize melanocortins. Such neutralizing anti-idiotypes or Fab fragments of such anti-idiotypes can be used in therapeutic regimens to neutralize the native ligand and treat $PGD_2$-related disorders, such as allergenic disorders and asthma.

Alternatively, antibodies to CRTH2 that can act as agonists of CRTH2 activity can be generated. Such antibodies will bind to the CRTH2 and activate the signal transducing activity of the receptor. In addition, antibodies that act as antagonist of CRTH2 activity, i.e. inhibit the activation of CRTH2 receptor would be particularly useful for treating $PGD_2$-related disorders, such as allergenic disorders, asthma, and inflammatory disorders.

Genetically engineered cells that express soluble CRTH2 ECDs or fusion proteins e.g. fusion Ig molecules can be administered in vivo where they may function as "bioreactors" that deliver a supply of the soluble molecules. Such soluble CRTH2 polypeptides and fusion proteins, when expressed at appropriate concentrations, should neutralize or "mop up" the native ligand for CRTH2, and thus act as inhibitors of CRTH2 activity and may therefore be used to treat $PGD_2$-related disorders, such as allergenic disorders, asthma, and inflammatory disorders.

CRTH2 is a cell surface protein present on certain T cells, brain, thymus, muscle, spleen, skin, and possibly other cell types, that appears respond to PGD2 released from mast cells, and possibly other cell types, an important early step in signal to be involved in PGD2-related disorders. As such, CRTH2 may be important early step in allergenic and inflammatory responses. Therefore, CRTH2 protein, analogs, derivatives, and fragments thereof, as well as nucleic acids (and sequences complementary thereto), and anti-CRTH2 antibodies, have uses in detecting and diagnosing such $PGD_2$-related disorders.

CRTH2 and CRTH2 nucleic acids can be used in assays to detect, prognose, or diagnose PGD2-related disorders that may result in chronic, acute, or abnormal allergenic and inflammatory responses, e.g., asthma.

The molecules of the present invention can be used in assays, such as immunoassays, to detect, prognose, diagnose, or monitor various conditions, diseases, and disorders affecting CRTH2 expression, or monitor the treatment thereof. In particular, such an immunoassay is carried out by a method comprising contacting a sample derived from a patient with an anti-CRTH2 antibody under conditions such that immunospecific binding can occur, and detecting or measuring the amount of any immunospecific binding by the antibody. In a specific aspect, such binding of antibody, in tissue sections, can be used to detect aberrant CRTH2 localization or aberrant (e.g., low or absent) levels of the CRTH2. In a specific embodiment, antibody to CRTH2 can be used to assay a patient tissue or serum sample for the presence of CRTH2 where an aberrant level of CRTH2 is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

CRTH2 genes and related nucleic acid sequences and subsequences, including complementary sequences, can also be used in hybridization assays. CRTH2 nucleic acid sequences, or subsequences thereof, comprising about at least 8 nucleotides, can be used as hybridization probes. Hybridization assays can be used to detect, prognose, diagnose, or monitor conditions, disorders, or disease states associated with aberrant changes in hspr expression and/or activity as described supra. In particular, such a hybridization assay is carried out by a method comprising contacting a sample containing nucleic acid with a nucleic acid probe capable of hybridizing to CRTH2 DNA or RNA, under conditions such that hybridization can occur, and detecting or measuring any resulting hybridization.

In specific embodiments, diseases and disorders involving decreased immune responsiveness during an infection or malignant disorder can be diagnosed, or their suspected presence can be screened for, or a predisposition to develop such disorders can be detected, by detecting decreased levels of CRTH2 protein, CRTH2 RNA, or CRTH2 functional activity (e.g., binding to $PGD_2$, anti-CRTH2 antibody-binding activity etc.), or by detecting mutations in CRTH2 RNA, DNA or CRTH2 protein (e.g., translocations in CRTH2 nucleic acids, truncations in CRTH2 gene or protein, changes in nucleotide or amino acid sequence relative to wild-type CRTH2) that cause decreased expression or activity of CRTH2. Such diseases and disorders include but are not limited to allergic and asthmatic disorders (e.g., allergic rhinitis, allergic asthma, bronchoconstriction), neurological disorders (including sleep disorders, and disorders in the regulation of body temperature or pain response) and inflammatory disorders (for example, rheumatoid arthritis, osteoarthritis, inflammatory bowel disease; disorders of the skin including psoriasis, eczema, erythema, pruritis, and acne; stroke, and any disease marked by reperfusion injury, graft rejection, and autoimmune diseases).

By way of example, levels of CRTH2 can be detected by immunoassay, levels of CRTH2 RNA can be detected by hybridization assays (e.g., Northern blots, in situ-hybridization), and CRTH2 activity can be assayed by measuring binding activities in vivo or in vitro. Translocations, deletions, and point mutations in CRTH2 nucleic acids can be detected by Southern blotting, FISH, RFLP analysis, SSCP, PCR using primers that preferably generate a fragment spanning at least most of the CRTH2 gene, sequencing of CRTH2 genomic DNA or cDNA obtained from the patient, etc.

In a preferred embodiment, levels of CRTH2 mRNA or protein in a patient sample are detected or measured relative to the levels present in an analogous sample from a subject not having the $PGD_2$-related disorder, such as an allergenic disorder, asthma, or inflammatory disorder. Decreased levels indicate that the subject may develop, or have a predisposition to developing, an allergenic disorder, asthma, or inflammatory disorder.

In a specific embodiment, levels of hsrp mRNA or protein in a patient sample are detected or measured, relative to the levels present in an analogous sample from a subject not having the disorder, in which increased levels indicate that the subject has, or has a predisposition to, an autoimmune disorder.

Kits for diagnostic use are also provided, that comprise in one or more containers an anti-CRTH2 antibody, and, optionally, a labeled binding partner to the antibody. Alternatively, the anti-CRTH2 antibody can be labeled (with a detectable marker, e.g., a chemiluminescent, enzymatic, fluorescent, or radioactive moiety). A kit is also provided that comprises in one or more containers a nucleic acid probe capable of hybridizing to CRTH2 RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a CRTH2 nucleic acid. A kit can optionally further comprise in a container a predetermined amount of a purified $PGD_2$ or CRTH2 nucleic acid, protein, derivative, analog, or fragment thereof, or, e.g., for use as a standard or control.

The invention encompasses methods and compositions for modifying the interaction with $PGD_2$ and CRTH2, and for treating $PGD_2$-related disorders, including, but not limited to, allergy, asthma, and inflammation. Because a loss of normal CRTH2 gene product function may result in the development of a $PGD_2$-related disorder phenotype, an increase in CRTH2 gene product activity, or activation of the CRTH2 pathway (e.g., downstream activation) would facilitate progress towards a normal $PGD_2$-related state in individuals exhibiting a deficient level of CRTH2 gene expression and/or CRTH2 activity.

Alternatively, symptoms of certain $PGD_2$-related disorders may be ameliorated by decreasing the level of CRTH2 gene expression, and/or CRTH2 gene activity, and/or down-regulating activity of the CRTH2 pathway (e.g., by targeting downstream signaling events). Different approaches are discussed below.

A CRTH2 antagonist can be used to treat conditions such as asthma or inflammation. Agonists of CRTH2 can be used to stimulate CRTH2 activity, in mammals in need of such treatment.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

EXAMPLE 1

The in vivo and in vitro assays described in this Example characterize the $PGD_2$/CRTH2 interaction, identifying $PGD_2$ as the key endogenous ligand for CRTH2.

Using 300-19 cells (transformed pre-B lymphocytes) expressing CRTH2, a number of mast cell and non-mast cell-derived mediators were screened in a $[Ca^{2+}]_i$ mobilization assay. (300-19 cells are disclosed in M. G. Reth et al., Nature, 317(6035), pp. 353–365, 1985). For the experiments herein, CRTH2 was expressed from a plasmid "p3.1 pro-lacflag" which contains ampicillin and neomycin resisitance markers, and is driven by the CMV promoter. A prolac signalling peptide allows membrane expression of the gene insert, with a Flag peptide tag at the N terminal permitting convenient detection of the expressed molecule. A preferred level of expression of CRTH2 is about 40,000 molecules/cell surface.

Calcium flux studies demonstrated that $PGD_2$ increased $[Ca^{2+}]_i$ mobilization in a CRTH2 stable cell line with an $EC_{50}$ of 15 nM. In contrast, PGJ2 had an $EC_{50}$ of 200 nM in this test, whereas other prostaglandins and their analogs (PGE2, PGF2α, BW-245C, and thromboxane mimetics) and leukotrenes were found to be inactive (with $EC_{50}$'s greater than 300 nM).

To directly determine the binding affinity of CRTH2 for $PGD_2$, the following binding assay was used. Transfected and parental 300-19 cells were washed twice at room temperature with assay buffer, and resuspended at a concentration of $2 \times 10^7$ cells/ml. Using a 96-well U-bottom polypropylene plate (Costar, Corning Inc., Acton, Mass.), the assay was set up as follows: 50 µl of vehicle (0.3% DMSO in assay buffer, total wells) or of 30 mM cold $PGD_2$ (NS wells); 50 µl cells ($2 \times 10^7$ cells/ml for $10^6$ cells per well); 50 µl 6 nM [3H]-$PGD_2$. The plate was allowed to incubate for 20 min at RT before centrifugation (2800 rpm, Sorval RT6000, 5 min, 4° C.). The plate was harvested (Packard Unifilter plate GF/C, previously soaked in 3% PEI for at least 1 hr) with cold assay buffer using a Packard Filtermate Cell Harvester (6×150 µl buffer wash per well). The filterplate was dried overnight. After the addition of 50 µl scintillation fluid (Packard Microscint 0), the plate was counted in a Packard Topcount scintillation counter (1 min per well). The $IC_{50}$ value for this binding has been determined to be 18 nM. The solutions of labeled $PGD_2$ and unlabeled "cold" $PGD_2$ were prepared as follows: 10 µl of [$^3$H]-$PGD_2$ (Amersham lot # TRK734 162 Ci/mmol, 0.1 Ci/ml in methanol: water: acetonitrile (3:2:1), 617 nM) per ml assay buffer was used to prepare a solution of [$^3$H]-PGD2 at a concentration of 6 nM (50 µl/well for final conc. of 2 nM); cold PGD2 (Biomol #PG-005, lot # P4653) was dissolved in DMSO for a stock of 10 mM (stored at −20° C.). The 10 mM stock was diluted 3:1000 to obtain a final concentration of 30 mM (50 µl/well for final conc. of 10 mM). Assay buffer: Hank's balanced saline supplemented with HEPES and sodium bicarbonate: 100 ml/L of 10× Hank's Balanced saline (with $Ca^{+2}$, $Mg^{+2}$); 10 ml/L of 1M HEPES; 4.7 ml/L of 7.5% Sodium Bicarbonate.

Figures 1A, 1B:
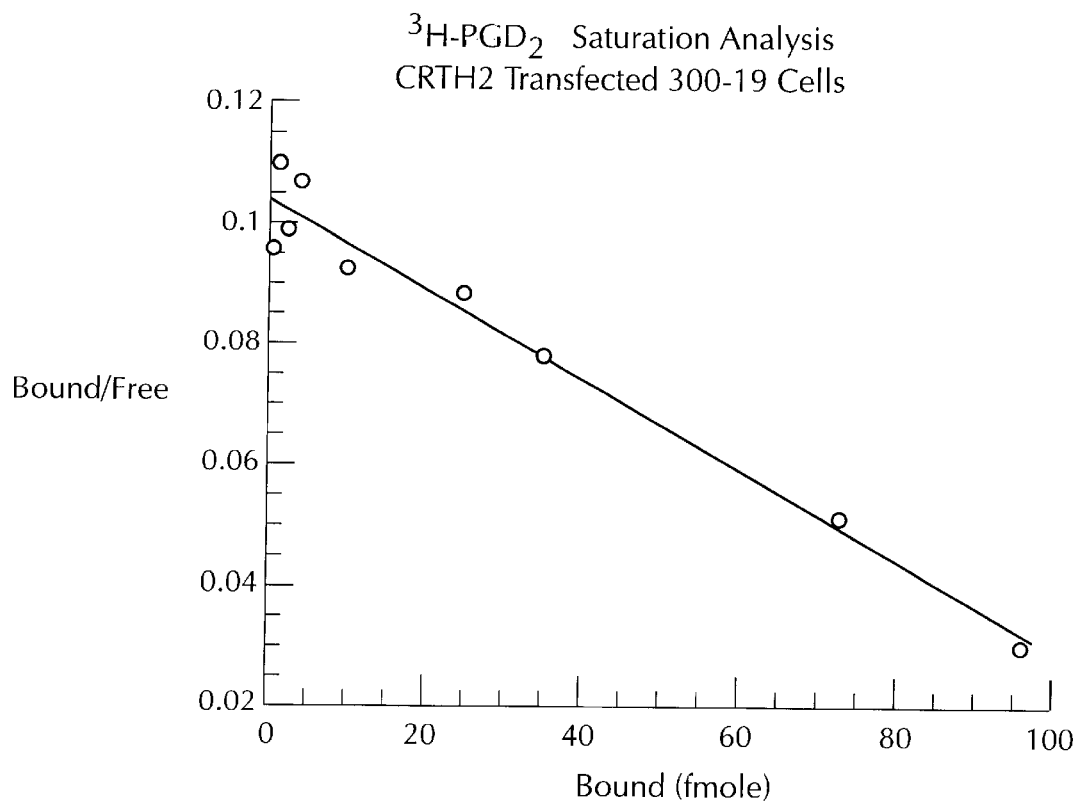
FIGS. 1A/B A. Scatchard plot analysis of the [$^3$H]-$PGD_2$ binding to cells transfected with CRTH2.

FIG. 1A shows a Scatchard plot analysis of the [$^3$H]-$PGD_2$ binding. This data indicated that the ligand bound to the transfectant with a homogenous population of receptors with a Kd=18.1 nM. The receptor concentration was calculated to be 79,554 sites/cell.

The ability of $PGD_2$ to bind CRTH2, and to stimulate a $PGD_2$ response in cells expressing CRTH2, was compared with that of other prostaglandins and prostaglandin analogs. First, prostaglandins and analogs were tested for their ability to compete with $PGD_2$ for binding to CRTH2, using competition binding studies. These studies indicated the following rank of agonist potency among the prostaglandins and analogs tested: $PGD_2$>>PGJ2>PGF2=PGE2>>BW245C. Next, comparative calcium release assays were performed. FIG. 1B shows the effects of the $PGD_2$, PGJ2, PGF2, PGE2, and BW245C on $[Ca^{2+}]_1$ mobilization in the transfectant. The order of $[Ca^{2+}]_1$ mobilization is similar to the order of their binding affinities as shown in FIG. 1B, i.e., $PGD_2$>PGF2a>>BW245C.

As is shown in FIG. 1B, the effects of the prostaglandins and analogs on human eosinophil [$^3$H]-$PGD_2$ binding site and eosinophil functional responses have the same order of potency (i.e., $PGD_2$>PGF2a>>BW245C). This agonist rank order of potency differs significantly from that of any known prostanoid receptors, and is consistent with their interactions with CRTH2 (see Table 1).

The amino acid sequence alignment of human CRTH2 with other prostaglandin receptors, DP, EP 1-4, TP, FP, and IP, can be determined from published sources. CRTH2 shows less than 30% sequence homology with the DP, EP 1-4, TP, FP and IP receptors.

Figure 3B:
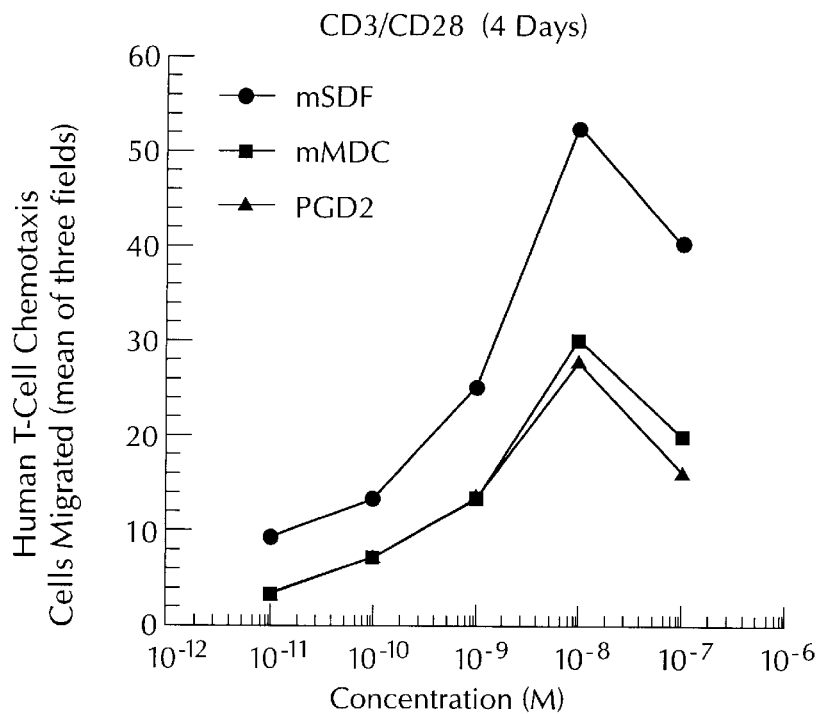

The chemotactic response of human T lymphocytes to $PGD_2$, murine MDC and murine mSDF was also assayed. Chemotaxis was determined using a 48-well Boyden chamber (Neuroprobe, Cabin John, Md.), and 3.0 µm polycarbonate filters. Cells were resuspended (3–3.5×10$^6$ cells/ml) in RPMI 1640 supplemented with 10 mM HEPES and 1 mg/ml bovine serum albumin (Sigma, St. Louis, Mo.), and placed into the upper wells of the chamber. The compound to be tested was placed in the lower wells. The chambers were incubated for 90–120 minutes at 37° C. in a humidified $CO_2$ incubator. At the end of the incubation period, the number of migrating cells on the filter (expressed per high power field) were enumerated microscopically. As shown in FIG. 3, both anti-CD3 stimulated T cells (upper panel) and anti-CD3 and anti-CD28—stimulated T cells respond specifically to $PGD_2$. In FIG. 4, the chemotactic response of human basophils to $PGD_2$ and C5a is shown.

TABLE 1

The effect of $PGD_2$ and other prostanoids on L3HIPGD2 binding and functional responses in isolated human eosinophils.

| Ligand | PGD2 binding $IC_{50}$ (uM) | ROS* release $EC_{50}$ (uM) | Chemotaxis $EC_{50}$ (uM) | Actin-polymer* $EC_{50}$ (uM) | $[Ca^{2+}]_i$ mobilization $EC_{50}$ (uM) |
|---|---|---|---|---|---|
| PGD2 | 0.025 (4) | 0.002 (6) | 0.003 (1) | 0.004 (4) | 0.03 (4) |
| PGJ2 | OT | 0.075 (1) | >0.1 (1) | 1.8 (1) | 0.13(2) |
| PGF2α | 1.5 (1) | >1 (3) | >0.1 (1) | 1.9 (1) | >1 (1) |
| BW-245C | >100 (3) | >1 (1) | >1 (1)?? | >1 (1)?? | >1 (1) |
| Pa, 11b-PGF2 | OT | >0.1 (2) | >0.1 (1) | >1 (2) | OT |
| PGE1 | OT | >0.1 (1) | >0.1 (1) | >100 (1) | >1 (1) |
| PGE2 | 3.3 (1)** | >0.1 (1)** | >0.1 (1)** | >300 (2)** | >1 (2)** |
| PGI2 | OT | >1 (2) | >0.1 (1) | >100 (1) | >1 (1) |
| U-46619 | OT | >0.1 (2) | OT | OT | >1 (1) |

*ROS: Reactive Oxygen Species; Actin-polymer: Human whole blood eosinophil actin-polymerization response
**Despite its binding to CRTH2, PGE2 fails to induce eosinophil response (i.e., actinpolymerization). It is hypothesized that PGE2 may blunt CRTH2-mediated eosinophil response by its binding to EP2 receptors (cAMP-mediated).

In connection with performing screens according to the practice of the present invention, it should be noted that the specific binding of $PGD_2$ to CRTH2 is higher at room temperature than at 40° C. In contrast, the specific binding of $PGD_2$ to the DP receptor is higher at 40° C. that at room temperature. It should also be noted that small concentrations of magnesium and calcium ions enhance the binding of $PGD_2$ to CRTH2, while slightly inhibiting binding thereof to the DP receptor. With respect to enhancing interaction of $PGD_2$ with the CRTH2 receptor, 5 mM of calcium or magnesium ions is a useful concentration, and generally between 1–50 mM, preferably 5–20 mM, will be of benefit.

EXAMPLE 2

The following experiments were performed to further characterize CRTH2, and to determine the role of CRTH2 in $PGD_2$-mediated inflammatory responses.

CRTH2 is a member of the 7-transmembrane G protein-coupled class of receptors. As a G protein-coupled receptor, CRTH2 is coupled through G-proteins to cytoplasmic mediated events. Interestingly, pertusis toxin inhibited $PGD_2$-mediated eosinophil chemotaxis, suggesting that CRTH2 probably links with Gi. Studies also indicated that CRTH2 uses calcium as the second messenger but not cAMP.

In humans, CRTH2 has a broad tissue distribution, it is expressed in the brain, thymus, muscle, spleen, skin and other tissues. It is thus possible that CRTH2 may have different effects in different tissues, activating a particular gene product or activity in one cell type, and downregulating the same or another gene product or activity in another tissue, depending on the signal transduction pathway activated in that particular cell type.

Given topically to guinea pig eyes, $PGD_2$ elicits ocular hypotension and a microvascular leakage followed by conjunctival inflammation (eosinophil infiltration, mucus secretion) at 6-hour post challenge (Woodward et al., 1990, Invest. Ophthalmol. Visu. Sci. 31:38–146). The ocular hypotension reaction was mimicked by BW-245C, whereas the microvascular leakage followed by conjunctival inflammation was BW-245C-insensitive, indicating that the inflammatory responses was mediated via another receptor, possibly CRTH2.

The CRTH2-mediated increase in vascular permeability may be a key component of cellular inflammation and this action can greatly facilitate the in vivo chemotactic response to a chemotactic factor. In dogs, tracheal instillation causes eosinophil accumulation in the lumen of their trachea at 1 to 4 hrs post challenge (Emery et al., 1989, Journal of Applied Physiology 67(3):959–62), and IV infusion produce a marked and rapid reduction in circulating eosinophils. In all of these studies there were no changes in neutrophil responses post $PGD_2$ challenge, an observation consistent with the lack of CRTH2 expression in neutrophils, and the fact that the radioligand receptor binding assay was not able to identify a specific binding site for 2 nM $[^3H]$-$PGD_2$ in purified human neutrophils.

In vitro studies with isolated human eosinophils demonstrated that activation of $[Ca^{2+}]_i$ mobilization, ROS release, actin-polymerization response and chemotaxis is most likely mediated via CRTH2 because of the similar rank orders of agonist potencies in these studies compared with those obtained in vitro from the $[^3H]$-$PGD_2$ binding study with CRTH2 transfectant (see Example 1). But eosinophil activation by $PGD_2$ is clearly not mediated through FP or TP receptors since PGF2ct or the known thromboxane mimetic U46619 do not show any activity in these assays. In addition to eosinophils, human activated T-lymphocytes and basophils were also responsive to $PGD_2$, and not to other prostanoids or BW-245C (see FIGS. 4 and 5) in chemotaxis assays.

Human activated T cells were demonstrated to respond to $PGD_2$, and that response to $PGD_2$ required the activation of T cells with CD3 and CD28. It is not yet known whether this response is restricted only to Th2 cells. Although CRTH2 was originally reported to be a Th2-specific receptor in human, studies in mice have indicated that both Th2 and Th1 cells express CRTH2 and respond to PGD2. These studies suggest that there may be some differences in the CRTH2 expression pattern between species.

$PGD_2$ has many other biological effects pertinent to allergy, asthma, and inflamation. For example, inhaled $PGD_2$ causes bronchoconstriction in asthmatics, which effect is 3.5x and 30x more potent than PGF2ct and histamine, respectively (Hardy et al., 1984, New England Journal of Medicine 311(4):209–13). This effect is preferential on peripheral rather than central airways (Wasserman et al., 1977, Prostaglandins 13(2): 255–69). Inhaled $PGD_2$ also causes coughing, and potentiates methacholine and histamine airway hyperreactivity in asthmatics. $PGD_2$ given intracutaneously to human skin elicits a strong erythema formation for up to 2 hours (Soter et al., 1983, Journal of Investigative Dermatology 80(2):115–9), reflecting an increase in venular permeability. Intranasal challenge of atopic and nonatopic subjects with $PGD_2$ causes a dose-dependent decrease in nasal patency, and increase in allergic symptoms (nasal congestion, cough and sore throat, in particular), thus mimicking pathophysiologies and symptoms associated with allergic rhinitis (Soter et al., 1983, Journal of Investigative Dermatology 80(2):115–9). In C57/BL mice, antigen- and compound 48/80-induced in skin itching is blocked by $PGD_2$ antagonists. However, because of the lack of a complete pharmacological characterization of these responses, it is not clear which prostanoid receptor (s) is involved. In vitro and in vivo studies suggest that the bronchoconstrictive response by $PGD_2$ could be partly due to a direct activation of airway smooth muscle TP receptor (Beasley et al., 1989, Journal of Applied Physiology 66(4) :1685–93) or an indirect stimulation of a prejunctional release of acetylcholine from airway parasympathetic nerves (Tamaoki et al., 1987, Journal of Applied Physiology 63(4) :1396–400). The former seems unlikely since $PGD_2$ binds to the TP receptor with a low affinity (Ki=75 uM); and the latter does not offer the information with regards to which prostanoid receptor is involved.

Modulators, i.e. antagonists and agonists of $PGD_2$ and CRTH2 interactions may also be important in treatment of pulmonary diseases. $PGD_2$ can function as a key mediator in allergy, asthma, and inflammation, and is one of the most abundant mediators produced by mast cells (besides histamine and peptidoleukotrienes), and is recovered from BAL of atopic asthmatics and nasal lavage from allergic rhinitis (Knani et al., 1992, Journal of Allergy & Clinical Immunology 90(6 Pt 1):880–9). In addition, patients with allergic rhinitis and asthma often do not get an effective relief of nasal congestion and pulmonary dysfunction even with the medications sold under the tradmarks ZYRTEC and SIGULAIR, indicating a mediator(s) other than histamine and leukotrenes is involved. It is possible that antigen-induced, mast-cell derived early release of $PGD_2$ may play a role in contributing to allergic symptoms as well as initiating inflammatory responses by recruiting eosinophils, lymphocytes and basophils into lungs. It appears that the BAL, and levels of $PGD_2$ and its metabolites in urine, are also significantly elevated after 12 hours post antigen challenge. Therefore, $PGD_2$ may also be involved in maintaining and potentially amplifying immune response by attracting more inflammatory cells.

Further kinetic studies revealed that anti-IgE triggers an early (2–30 min) and late (4–6 hrs) production of $PGD_2$ where the former is controlled by COX-1 and the later is regulated by inducible COX-2 (Reddy et al., 1999, Biochemical & Biophysical Research Communications 265(1): 205–10). In fact, human Th2 cells and activated alveolar macrophages have recently been shown to synthesize PGD2 by a COX-2 dependent pathway (Tamaoki et al., 1987, Journal of Applied Physiology 63(4):1396–400; MacDermot et al., 1984, Prostaglandins 27(2):163–79). Immunohistochemistry studies show a significant increase in bronchial epithelium and submucosal cellular expression of COX-2, but not of COX-1 in asthmatics (Sousa et al., 1997, Thorax 52(11): 940–5). Since the kinetics of $PGD_2$ production is temporally correlated with early and late phase responses seen in antigen-challenged asthmatics, it is expected that mast cells, Th2 cells and activated alveolar macrophages are cell types that contribute to the surge of the levels of $PGD_2$ in the late phase.

EXAMPLE 3

FIG. 2 presents results of the calcium flux assay (again using 300–19 CRTH2 transfectants) for close analogs of $PGD_2$.

EXAMPLE 4

Additional Assay to Measure Binding of $PGD_2$ Agonists and Antagonists to CRTH2

The binding of $PGD_2$ agonist and antagonist compounds was also measured using membranes prepared from CRTH2-expressing L1.2 cells. To make the membrane preparation, 10 grams of cell pellet are resuspended in 20 ml of cold 50 mM Tris HCl (pH 7.7), and homogenized three times (10 seconds each) on ice with a Polytron tissue homogenizer. The suspension is then diluted to 80 ml with the same buffer, and centrifuged at 40,000×g for 30 min. After discarding the supernatant, the pellet is washed once with cold 80 mM Tris HCl (pH 7.7) by repeating the resuspension, homogenization, and centrifugation described above. Finally, the pellet is resuspended in 20 ml of cold 50 mM Tris HCl (pH 7.7), aliquoted, and stored at −80° C. On the day of the assay, the membranes are thawed on ice, and 25 ul is placed into each well of a 96-well microtiter plate. 5 ul of 0.5 M $MgCl_2$ and 10 ul of PVT-WGA scintillation proximity assay (SPA) beads (Amersham) are then added to each well and mixed thoroughly. 5 ul of the compounds to be tested are then added, followed by 5 ul of 30 nM $^3H$-$PGD_2$(200 Ci/mmol from NEN diluted 1:17) to initiate the binding reaction. The plate is then sealed and incubated at room temperature for at least 1 hour before being counted on a Wallac Microbeta Trilux scintillation counter. Non-specific binding is measured in wells containing 100 uM unlabeled $PGD_2$. Active compounds are able to compete with $^3H$-$PGD_2$ for binding to CRTH2 and are identified by a decrease in the number of cpm bound.

EXAMPLE 5

Additional Assay to Measure Functional Activity (Agonist Versus Antagonist) of Compounds at CRTH2

The functional activity of compounds was measured by their ability to block the transient $Ca^{2+}$ flux induced by $PGD_2$ in L1.2 cells expressing CRTH2. The $Ca^{2+}$ flux is measured with the FLIPR by using the FLIPR Calcium Assay Kit (Molecular Devices). First, a 1× solution of the Reagent Buffer is made by diluting Component B from the kit 1:10 and adjusting the pH to 7.4 with NaOH. Second, the $Ca^{2+}$ Sensing Dye is prepared by dissolving 1 vial of Component A from the kit in 10 ml of 1× Reagent Buffer. On the day of the assay, 20 ml of 1× Reagent Buffer is mixed with 20 ml of Dulbecco's Modified Eagle Media (DMEM), 400 ul of 250 mM probenecid, and 1 ml of the $Ca^{2+}$ Sensing Dye solution to produce the Assay Buffer. Cells are then pelleted by centrifugation at 1000×g for 5 minutes, and approximately 90% of the old culture media is removed by aspiration. The cells are then resuspended in Assay Buffer to a concentration of $3.3 \times 10^3$ cells/ul, and 60 ul of this suspension is placed into each well of a 384-well plate. The cell plate is incubated at 37° C. for 1 hour in 5% $CO_2$, and then 5 ul of the compounds to be tested are added. The cell plate is then placed into the FLIPR along with a plate containing 1.4 uM $PGD_2$. The FLIPR automatically adds 5 ul of $PGD_2$ (the final concentration is 100 nM) to the cell plates, and measures the subsequent $Ca^{2+}$ flux over a period of 2 minutes. Compounds that are able to inhibit the production of this $Ca^{2+}$ flux are antagonists.

EXAMPLE 6

The compounds depicted in FIGS. 7A/B, based on the PGD ring, were tested for selectivity for the CRTH2 receptor (in comparison with DP).

In the assay, the capacity of each D-ring compound to compete with binding of $^3$H-PGD$_2$ was measured at both the CRTH2 and DP receptors, and an IC$_{50}$ value (in μM) was determined. In the controls, using cold PGD$_2$ to compete with $^3$H-PDG$_2$, the IC$_{50}$ value of 0.0107 was determined (8 trials) at CRTH2, and a value of 0.0234 was determined at the DP receptor (7 trials). The binding assay procedure of Example 1 was used. Preferably, the ratio of IC$_{50}$ at CRTH2 to IC$_{50}$ at DP is less than about twenty, and more preferably is less than about two hundred.

The compounds 13,14-dihydro-15-keto PGD$_2$; 15(R)15-methyl PGD$_2$; and 15-deoxy-delta 12, 14, PGD$_2$ were particularly selective for CRTH2. The compounds depicted in FIGS. 7A/B were determined to be PGD$_2$ agonists in separate assays.

EXAMPLE 7

The compounds depicted in FIG. 8, based on the PGF ring, were similarly tested, and showed selectivity for the CRTH2 receptor (in comparison with DP). The compounds depicted in FIG. 8 were determined to be PGD$_2$ agonists in separate assays.

EXAMPLE 8

The compounds depicted in FIG. 9, based on the PGJ ring, were similarly tested for selectivity for the CRTH2 receptor (in comparison with DP). The compounds depicted in FIG. 9 were determined to be PGD$_2$ agonists in separate assays.

EXAMPLE 9

The four compounds, (a) to (d), depicted in FIG. 10 were similarly tested for selectivity for the CRTH2 receptor (in comparison with DP). The compounds were determined to be PGD$_2$ antagonists in separate assays (see Example 5).

With respect to synthesis of the compounds of this Example, the first compound, FIG. 10(*a*), was reported in the chemical literature (Sindelar, K. et al.; Collect. Czech. Chem. Commun., 40, pp. 3530–3544, 1975) and its synthesis is straightforward.

The methyl ester of the steroid compound of FIG. 10(*b*) has been prepared (see I. G. Reshetova et al., Bull. Acad. Sci. USSR Div. Chem. Sci. (English Translation), 39; 3.2; pp. 607–609, 1990; and also Izv. Akad. Nauk SSSR Ser. Khim.; RU; 3; pp. 687–690, 1990).

Compound 3, FIG. 10(*c*), may be synthesized via a route analogous to that described in C. Menciu et al., J.Med.Chem.; 42(4), pp. 638–648, 1999.

Compound 4, FIG. 10(*d*), is synthesized as described in B. L. Mylari et al., J. Med. Chem.; 34; pp.108–122, 1991.

What is claimed is:

1. A method for identifying a compound that modulates the binding of PGD$_2$ to CRTH2 receptor comprising:
   (a) contacting a sample of CRTH2 with PGD$_2$ and measuring the binding of PGD$_2$ thereto;
   (b) contacting a similar sample of CRTH2 with both PGD$_2$ and also an appropriate amount of a test compound, and measuring the binding of PGD$_2$ to said CRTH2; and
   (c) comparing the results in (a) and (b) to determine if the binding of PGD$_2$ is affected by the presence of said test compound.

2. A method for identifying a compound that modulates an activity of CRTH2 receptor that is normally dependent upon the binding of PGD$_2$ thereto, comprising the steps of:
   (a) contacting a sample of CRTH2 with PGD$_2$ and measuring a resultant activity of said CRTH2;
   (b) contacting a similar sample of CRTH2 with PGD$_2$ in the presence of an appropriate amount of a test compound, and measuring said resultant activity of CRTH2; and
   (c) comparing the results in (a) and (b) to determine if the PGD$_2$-dependent activity of CRTH2 is affected by the presence of said test compound.

3. The method of claim 2, in which the results obtained in step (c) determine that the test compound is an antagonist that interferes with the PGD$_2$dependent activity of CRTH2.

4. The method of claim 2, wherein the test compound is an antibody specific for CRTH2.

5. The method of claim 2, wherein the test compound is an antibody is specific for PGD$_2$.

6. The method of claim 2, in which the results obtained in step (c) determine that the test compound is an agonist that enhances the PGD$_2$-dependent activity of CRTH2.

7. The method of claim 2, wherein said CRTH2 is present on the surface of a mammalian cell, on a membrane fragment thereof, or on a lipid vesicle.

8. The method of claim 7, wherein the CRTH2 is present on the surface of a mammalian cell, and the PGD$_2$-dependent activity of said CRTH2 is the chemotactic response of said cell to PGD$_2$.

9. The method of claim 7, wherein the CRTH2 is present on the surface of a mammalian cell, and the PGD$_2$-dependent activity of CRTH2 is an affect on (a) intracellular Ca$^{2+}$ concentration, (b) the release of reactive oxygen species, or (c) an affect on actin polymerization.

10. The method of claim 2 wherein the CRTH2 is immobilized to a solid surface.

11. The method of claim 10 wherein said solid surface is a microtiter dish.

* * * * *